United States Patent
Eberhard et al.

(10) Patent No.: US 7,110,490 B2
(45) Date of Patent: Sep. 19, 2006

(54) FULL FIELD DIGITAL TOMOSYNTHESIS METHOD AND APPARATUS

(75) Inventors: Jeffrey Wayne Eberhard, Albany, NY (US); Bernhard Erich Hermann Claus, Niskayuna, NY (US); Cynthia Elizabeth Landberg, Clifton Park, NY (US); Serge Louis Wilfrid Muller, Guyancourt (FR); Reinhold Franz Wirth, Ballston Spa, NY (US); Yann Delmas, Coubevoie (FR); James George Morrow, Wauwatosa, WI (US)

(73) Assignee: General Electric Company, Niskayuna, NY (US)

( * ) Notice: Subject to any disclaimer, the term of this patent is extended or adjusted under 35 U.S.C. 154(b) by 314 days.

(21) Appl. No.: 10/248,007

(22) Filed: Dec. 10, 2002

(65) Prior Publication Data

US 2004/0109529 A1    Jun. 10, 2004

(51) Int. Cl.
*G21K 1/12* (2006.01)
*H01G 1/02* (2006.01)
(52) U.S. Cl. .................... 378/23; 378/25; 378/197
(58) Field of Classification Search .............. 378/20, 378/4, 901, 21–27, 196, 197
See application file for complete search history.

(56) References Cited

U.S. PATENT DOCUMENTS

| | | | |
|---|---|---|---|
| 5,485,500 A | 1/1996 | Baba et al. | |
| 5,872,828 A | 2/1999 | Niklason et al. | |
| 6,196,715 B1 | 3/2001 | Taguchi et al. | |
| 6,292,531 B1* | 9/2001 | Hsieh | 378/37 |
| 6,341,156 B1* | 1/2002 | Baetz et al. | 378/98.8 |
| 6,389,100 B1* | 5/2002 | Verman et al. | 378/84 |
| 6,483,891 B1* | 11/2002 | Lazarev et al. | 378/37 |
| 6,748,046 B1* | 6/2004 | Thayer | 378/22 |
| 6,960,020 B1* | 11/2005 | Lai | 378/207 |
| 2002/0168053 A1 | 11/2002 | Schomberg | |

FOREIGN PATENT DOCUMENTS

| | | |
|---|---|---|
| DE | 10016678 | 10/2001 |
| WO | 0057788 | 10/2000 |
| WO | 03020114 | 3/2003 |

OTHER PUBLICATIONS

X-Ray Optical Systems Inc.—Technology—www.xrayoptics.com.
European Search Report.

* cited by examiner

*Primary Examiner*—Edward J. Glick
*Assistant Examiner*—Irakli Kiknadze
(74) *Attorney, Agent, or Firm*—Fletcher Yoder

(57) ABSTRACT

A tomosynthesis system for forming a three dimensional image of an object is provided. The system includes an X-ray source adapted to irradiate the object with a beam of X-rays from a plurality of positions in a sector, an X-ray detector positioned relative to the X-ray source to detect X-rays transmitted through the object and a processor which is adapted to generate a three dimensional image of the object based on X-rays detected by the detector. The detector is adapted to move relative to the object and/or the X-ray source is adapted to irradiate the object with the beam of X-rays such that the beam of X-rays follows in a non arc shaped path and/or a center of the beam of X-rays impinges substantially on the same location on the detector from different X-ray source positions in the sector.

55 Claims, 14 Drawing Sheets

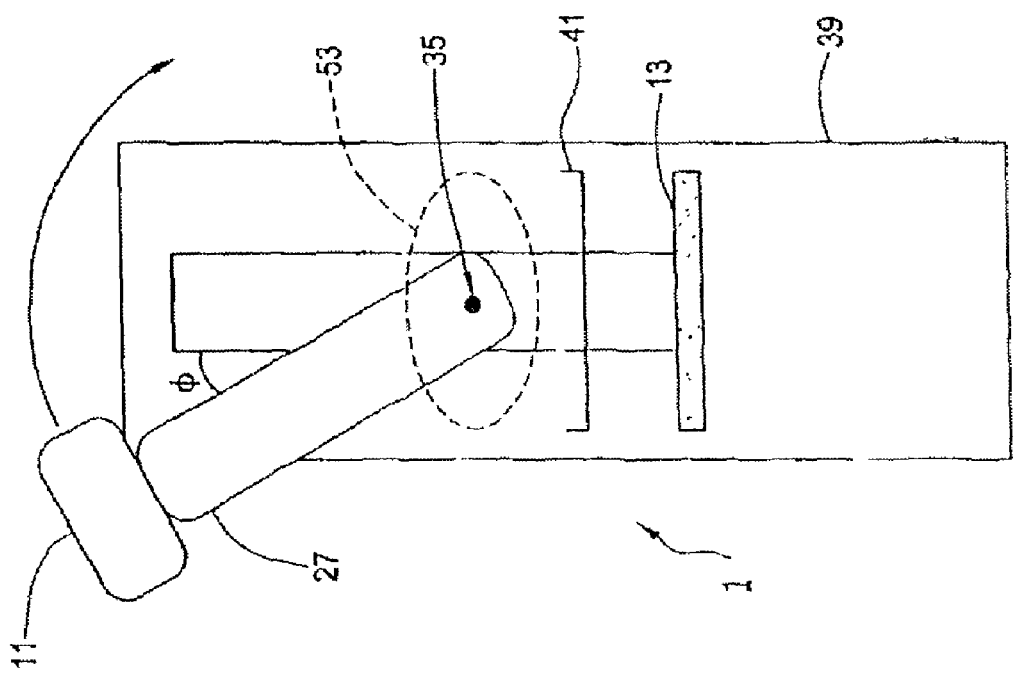

FULL FIELD DIGITAL TOMOSYNTHESIS METHOD AND APPARATUS

BACKGROUND OF THE INVENTION

The present invention relates generally to an imaging system, and more particularly to an X-ray tomosynthesis mammography imaging system.

X-ray motion tomography is an X-ray imaging method in which an X-ray tube and a detector move in opposite directions relative to a patient or another object that is being imaged. In tomography, X-rays beams are turned on while the X-ray tube and the detector are in motion, thereby selecting a single in-focus plane and blurring out all others. However, tomography is used to image only a single in-focus slice of the object being imaged rather than a three dimensional volume of the object being imaged. To image other slices of the object, additional scans of the X-ray tube and detector are needed. If a human patient is being imaged, repeated scans cause an undesirably high X-ray exposure dose for the patient.

X-ray mammography is the modality of choice for breast cancer screening. U.S. Pat. No. 5,872,828 incorporated by reference in its entirety describes a tomosynthesis system for breast imaging. This system produces a three dimensional image of the breast being imaged from a single scan of the X-ray source in an arc shaped path. The tomosynthesis system contains an X-ray source which moves in an arc shaped path over the breast that is being imaged, a stationary digital X-ray detector and an image processor. The detector is mounted on a stationary portion of a support structure. The X-ray source is mounted on a movable portion of the support structure. The movable portion of the support structure is an arm whose lower end is rotatably attached to the stationary support structure at a pivot point, and whose upper end supports the X-ray source.

However, while this tomosynthesis system is capable of forming adequate three dimensional mammography images, it suffers from several disadvantages. In order to obtain a three dimensional image of the breast, the image that is formed from the rotation of the X-ray source in an arc shaped path is mathematically transformed to construct an approximation of an image that would have resulted as if the X-ray source moved in a line shaped path parallel to the detector plane. Thus, the image for each tomographic plane is transformed to approximate an image that would have been formed based on the so-called Twinning principle. A three dimensional image of the breast is then reconstructed from the individual reconstructed images of tomosynthesis planes based on the Twinning principle. This algorithm adds complexity to the image processing.

Furthermore, the X-ray source is subject to a large amount of vibration because the system operates in a "step and shoot" mode, which distorts and blurs the image. In this mode, the X-ray source is off during its movement along the arc shaped path and is on during stops along the path. Thus, the X-ray source moves along the path, then stops, emits an X-ray beam (i.e., emits a shot) and then continues to move. The start and stop motion of the X-ray source causes the X-ray source to vibrate during the sudden stops, which causes the X-ray beam to be displaced relative to the object and to increase the blurring of the image. Thus, a plurality of projection images from a plurality of projection angles are formed. The range of the projection angles is less than 180 degrees. Thus, the X-ray source moves in an arc shaped path in a plane of a sector of a sphere, as opposed to moving 180 to 360 degrees around the patient.

BRIEF SUMMARY OF THE INVENTION

In accordance with one preferred aspect of the present invention, there is provided a tomosynthesis system for forming a three dimensional image of an object, comprising an X-ray source adapted to irradiate the object with a beam of X-rays from a plurality of positions along a path in a sector, an X-ray detector positioned relative to the X-ray source to detect X-rays transmitted through the object, and a processor which is adapted to generate a three dimensional image of the object based on X-rays detected by the detector. The detector is adapted to move relative to the object, or the X-ray source is adapted to irradiate the object with the beam of X-rays such that a focal point of the beam of X-rays follows a non arc shaped path, or a center of the beam of X-rays impinges substantially on the same location on the detector from different X-ray source positions in the sector.

In accordance with another preferred aspect of the present invention there is provided a tomosynthesis system for forming a three dimensional image of an object, comprising an X-ray source adapted to periodically irradiate the object with a beam of X-rays, wherein the X-ray source is adapted to emit the beam of X-rays while moving in a first direction along a path in a sector, an X-ray detector positioned relative to the X-ray source to detect X-rays transmitted through the object, and a processor which is adapted to generate a three dimensional image of the object based on X-rays detected by the detector. The detector is adapted to move in a second direction opposite to the first direction while the X-ray source moves in the first direction and the X-ray source emits the beam of X-rays.

In accordance with another preferred aspect of the present invention, there is provided a tomosynthesis system for forming a three dimensional image of an object, comprising at least two X-ray sources adapted to irradiate the object with beams of X-rays from a plurality of positions along a path in a sector, an X-ray detector positioned relative to the at least two X-ray sources to detect X-rays transmitted through the object, and a processor which is adapted to generate a three dimensional image of the object based on X-rays detected by the detector.

BRIEF DESCRIPTION OF THE DRAWINGS

FIGS. 11–14 are schematic illustrations of the alternative systems according to the preferred embodiments of the invention.

DETAILED DESCRIPTION OF THE INVENTION

The present inventors have realized that if the X-ray detector moves suitably relative to the imaged object and/or if the X-ray source irradiates the imaged object with a beam of X-rays such that the focal spot of the beam of X-rays follows a non arc shaped path relative to the detector, an improved quality tomosynthesis image with less blurring can be obtained. The focal spot of the beam of X-rays may follow the non arc shaped path by suitably moving the X-ray source, by shifting an electron beam focal spot on an X-ray target in the X-ray source and/or by using X-ray beam directing optics. Furthermore, an improved quality image is obtained if two or more X-ray sources are used. The preferred embodiments of a tomosynthesis system and method will now be described in detail. Each embodiment may be used independently or with any one or more other embodiments described below.

Figure 1:
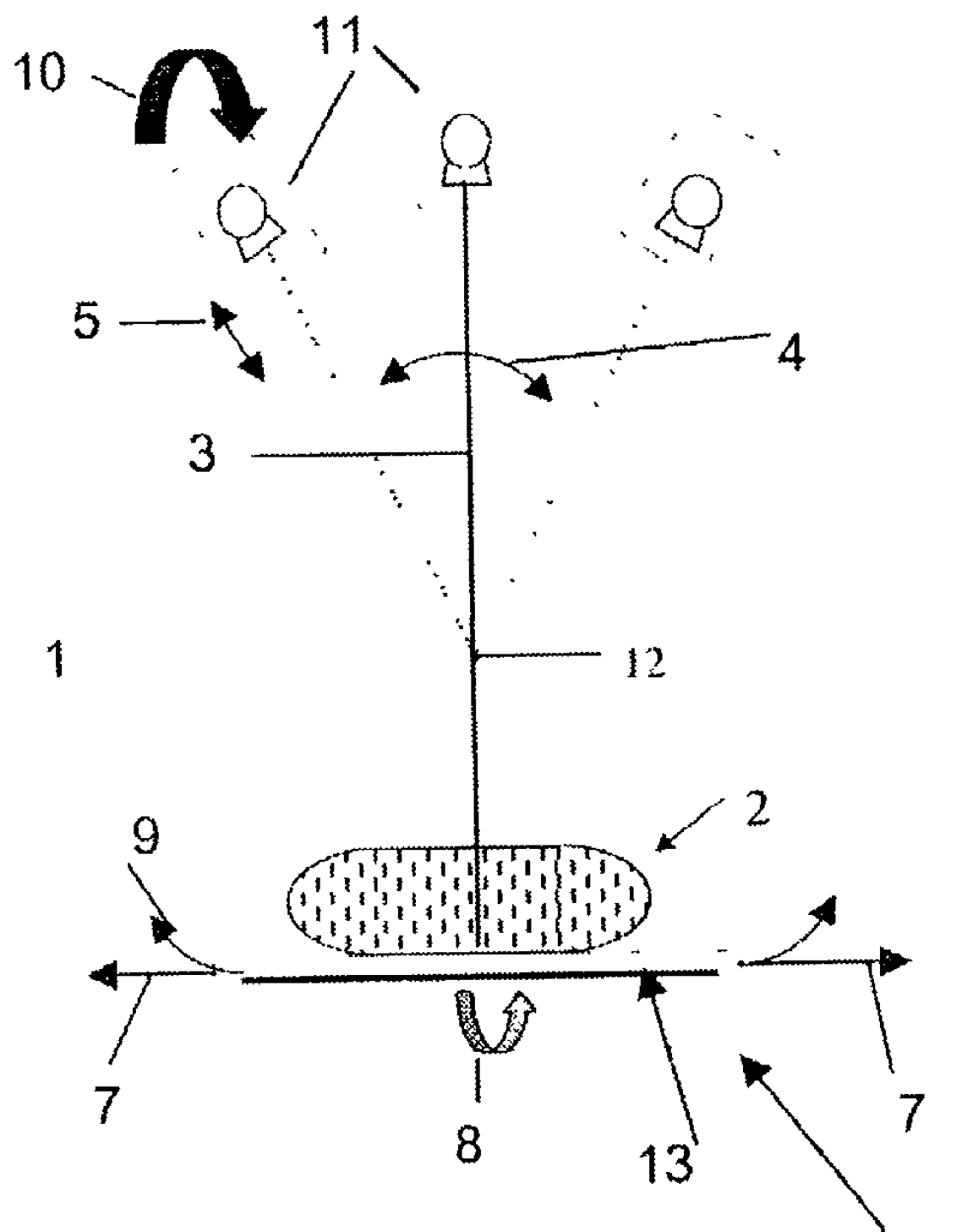
FIGS. 1, 4–6 and 8 are schematic front view illustrations of the systems according to the preferred embodiments of the invention.
Figure 2:
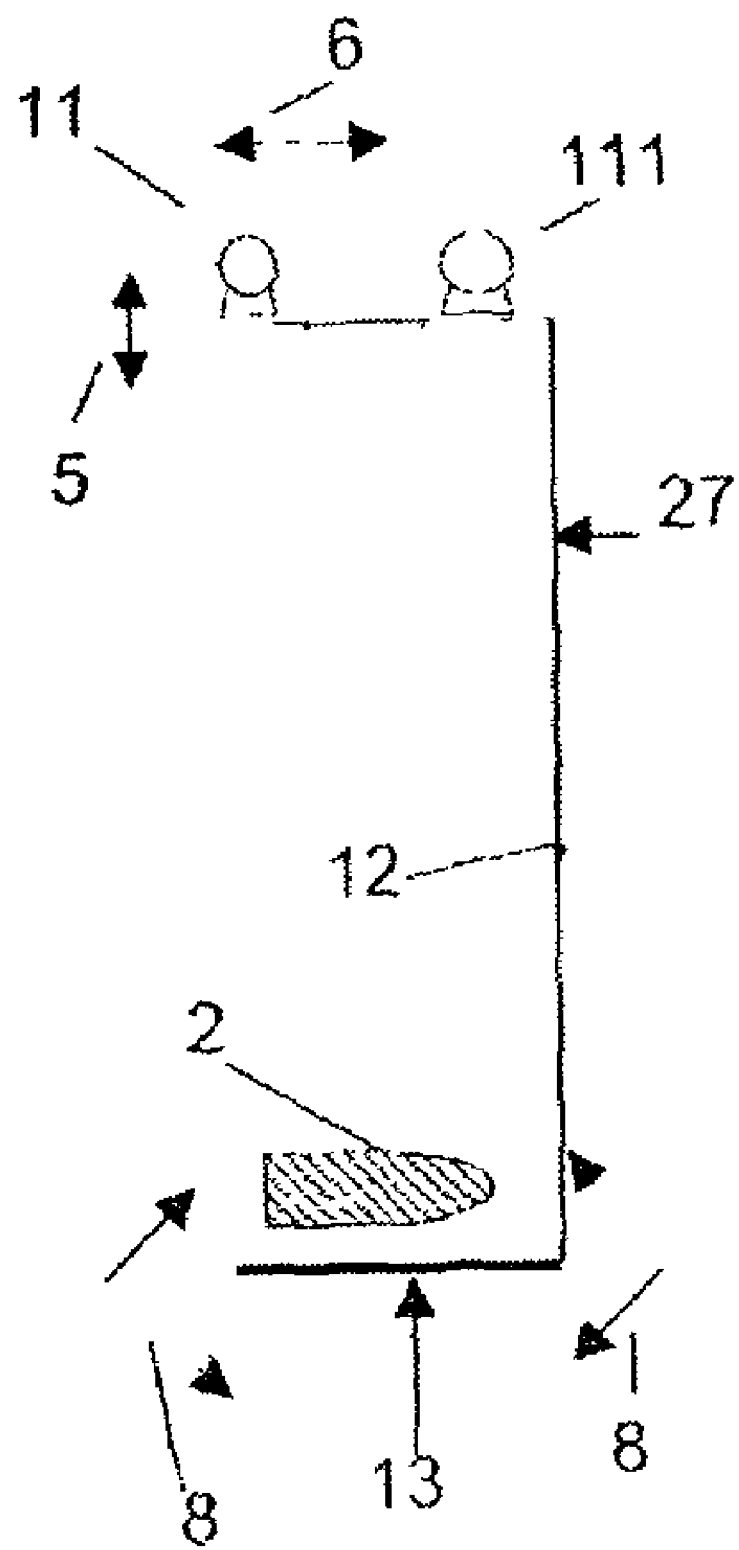
FIG. 2 is a schematic side view illustration of the system of FIG. 1
Figure 3:
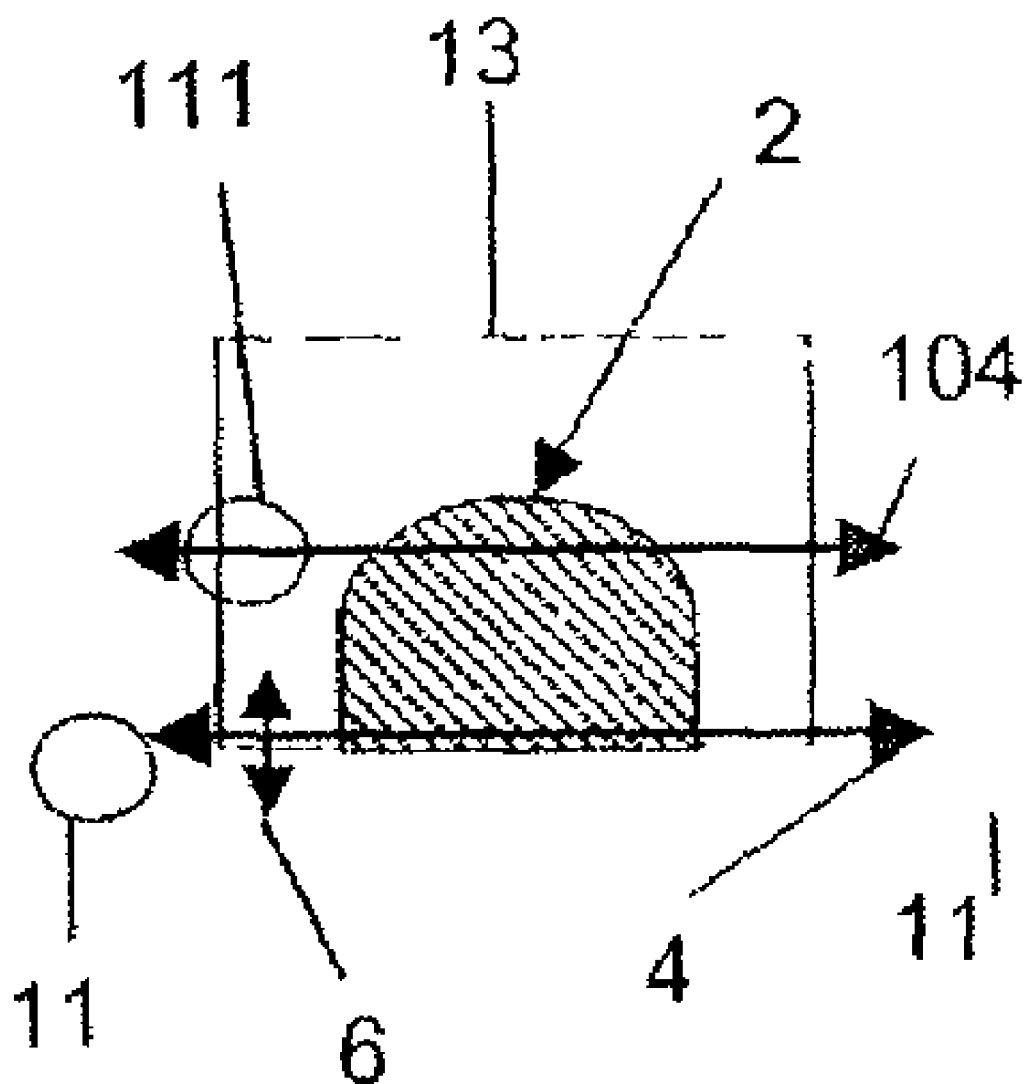
FIG. 3 is a schematic top view illustration of the system of FIG. 1.

FIG. 1 schematically illustrates a front view of a tomosynthesis system 1 used to form a three dimensional image of an object 2. FIG. 2 illustrates a side view and FIG. 3 illustrates a top view of this system 1. Preferably, the system 1 is a mammography system used to image human breasts. However, the system 1 may also be used to image inanimate objects, other human body parts or animal body parts.

The system 1 includes an X-ray source 11. The X-ray source 11 preferably comprises an X-ray tube located inside a housing. The X-ray source described in U.S. Pat. No. 5,872,828 rotates in an arc shaped path in one plane of a sector of a sphere. The arc shaped path appears as an arc in the front view and as a straight line in the top view. Therefore, the X-ray source 11 shown in FIG. 1 may rotate in an arc shaped path in one plane. However, in some preferred aspects of the present invention, in addition to rotating about an axis of rotation 12, along an arc shaped path 4, the X-ray source 11 may also move in a radial direction 5 (i.e., direction along the column or arm 27 which supports the source 11), which will be referred to as the "r" direction and/or the source 111 may move out of the rotation plane in direction 6, (i.e., in a direction from patient's chest wall to the support arm or column, or in the opposite direction), which will be referred to as the "y" direction. The axis of rotation 12 may be at different heights above the detector, and is preferably near the height of the detector surface. Motion in the r and y directions will cause the source 11 to move in an non-arc shaped path, because motion in the r direction will cause the path to have a non-arc shape in the front view, and motion in the y direction will cause the path to have a non-linear shape in the top view. Thus, rotation of the X-ray source 11 in the arc shaped path 4 in a rotation plane with optional r and/or y direction movement during the rotation cycle is generically referred herein as movement or rotation in a sector, such as a sector of a circle or a sphere. With varying r, the X-ray source moves in a region bounded by two spheres of different radius, and bounded by a maximum angular range. As defined herein, this movement is included in the rotation within a sector. Thus, the X-ray source irradiates the object 2 with a beam of X-rays 3 from a plurality of positions in a sector (i.e., from some but not all positions along the path in the sector).

An X-ray detector 13 is positioned relative to the X-ray source 11 to detect X-rays 3 transmitted through the object 2. The system 1 also preferably contains a processor, such as a computer or a special purpose microprocessor, which generates a three dimensional image of the imaged object based on X-rays 3 detected by the detector 13 from a scan of the X-ray source 11 in the sector.

In a first preferred embodiment of the invention, the detector 13 moves relative to the object 2 being imaged. The detector 13 may be moved by any suitable moving mechanism. Preferably, the detector 13 is located within a detector housing or image receptor 14 and is moved by a piezoelectric actuator. Alternatively, the detector may be moved by a mechanical actuator, such as a movable plate or the detector may be moved on a rail with a ball screw or other suitable pushing or pulling mechanism. The detector 13 may be moved in one or more desired directions described below.

In a first preferred aspect of the first preferred embodiment of the invention, the detector 13 is translated inside the housing 14 in a linear path 7 below the object 2 being imaged. In other words, the detector 13 is translated left and right as shown by arrows 7 in FIG. 1. Preferably, the housing 14 is wider than the detector 13. For example, the housing 14 may be 3–9 cm, such as 6 cm wider than the detector 13 (i.e., 3 cm wider on each side), which allows significant motion of the detector 13 within housing 14. However, smaller motion of the detector, such as 5 to 60 micron motion may be preferable in some instances.

One advantage of the translation of the detector 13 is a reduction in truncation in the projection images by synthesizing a larger effective detector aperture. Thus, the X-ray source 11 rotates in an arc shaped path in a first direction (such as to the right along path 4 in FIG. 1) relative to the object 2. The X-ray source 11 periodically emits a beam of X-rays 3 at positions on the arc shaped path 4. The timing of when the source 11 emits an X-ray beam 3 may be controlled either by the position of the source on the path, by timing, for example at predetermined times during the scan, or by system capability, such as when all components are "ready", or any combination thereof. For example, FIG. 1 illustrates the X-ray source 11 emitting an X-ray beam 3 from three positions. Preferably, the X-ray source 11 emits X-ray beams 3 from seven to thirty one, such as eleven or twenty one positions on the arc shaped path 4. While the X-ray source 11 rotates in a first direction (i.e., to the right) along path 4, the detector 13 moves in a path 7 in a second direction (i.e., to the left) opposite to the first direction. Preferably, path 7 is located in a plane, and may be a linear path if desired. In one embodiment in particular, if the path of the focal spot of the X-ray beam includes a component in the y-direction, as explained in more detail below, the path of the detector may also include a component in the y-direction, but opposite of the movement of the focal spot of the X-ray beam. If desired, the X-ray source 11 may be moved in a non arc shaped path instead, as will be described in more detail with respect to the second preferred embodiment.

Translating the detector 13 in an opposite direction from the rotation direction of the X-ray source 11 allows the detector 13 to be generally opposite of the X-ray source with respect to the imaged object 2 and allows the X-ray beams 3 to be incident on the detection surface of the detector 13. Thus, in the first preferred aspect of the first embodiment, the detector 13 is translated incrementally in the second direction along path 7 while the X-ray source 11 moves incrementally in the first direction along path 4, to ensure that the X-ray beam 3 is always incident on the detector 13 surface. Before a new image acquisition, and after a previous image acquisition, the detector 13 and the X-ray source 11 move to suitable start positions. In this embodiment, the detector 13 and the X-ray source 11 preferably remain stationary while the X-ray source 11 emits a shot (i.e., a beam of X-rays 3 such that the system 1 operates in the "step and shoot" mode). The detector 13 and the X-ray source 111 move between the X-ray shots. Furthermore, if desired, the detector 13 may be moved during the X-ray shot in addition to or instead of being moved between the X-ray shots.

In a second preferred aspect of the first embodiment, the system 1 operates in a "continuous" mode rather than in a "step and shoot" mode. In a continuous mode, the X-ray source 11 emits the X-ray beam 3 (i.e., a shot) while the X-ray source is in motion in the first direction along path 4. The continuous mode of operation reduces vibration blurring in the image that results from the rapid acceleration and deceleration of the X-ray source required in the step and shoot mode. In other words, the blurring in the step and shoot mode occurs due to X-ray source 11 shaking from the rapid deceleration which precedes the shot, which causes the X-ray beam 3 to wobble. To reduce the vibration blurring, the overall speed of the X-ray source may be decreased or the system may be operated in the continuous mode, where the X-ray source 11 moves during the X-ray shot, albeit usually at a slower velocity than during the period when the X-ray source is off. In one alternative aspect of the second embodiment, the detector 13 is stationary during each shot while the source 11 is moving.

However, the motion of the X-ray source during the X-ray shot reduces vibration blurring, but introduces motion blurring. The magnitude of motion blurring is usually smaller than the magnitude of vibration blurring in the step and shoot mode. Therefore, total blurring can be decreased in the continuous mode. For a stationary detector, the maximum motion blurring usually occurs for imaged portions of the top of the imaged object 2. An example of motion blurring is illustrated in FIG. 4.

Figure 4:
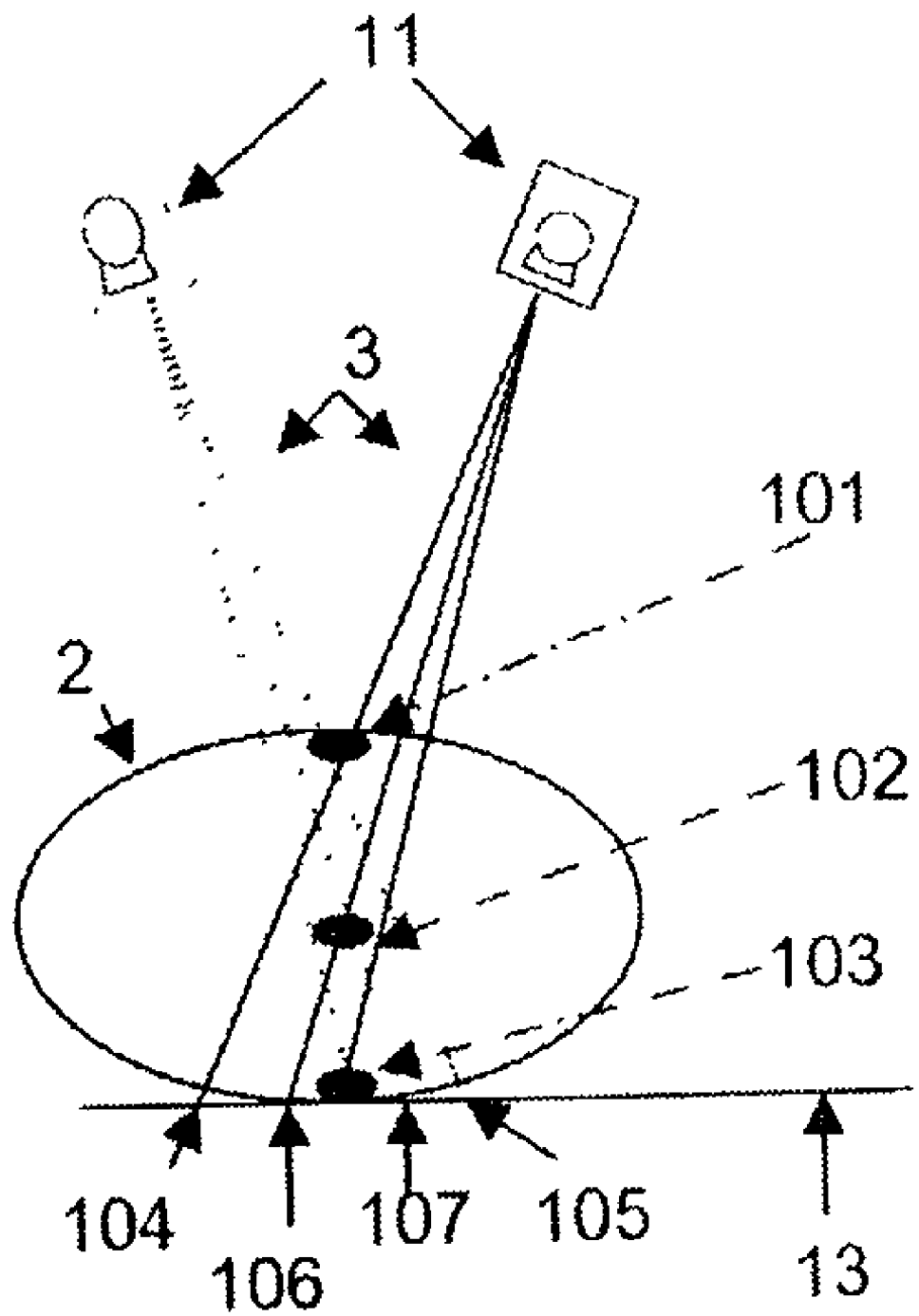

FIG. 4 illustrates an object to be imaged 2 containing a first point 101, 9.5 cm from the detector 13, and 56.5 cm from the X-ray tube of the X-ray source 11. Thus, dividing 56.5 by 9.5 results in a magnification of 6. The object 2 also contains a second point 102 at its mid-point, 4.5 cm from the detector 13, and a third point 103 right at the upper detector 13 surface (i.e., about 0 cm from the detector). The system position and orientation is assumed to be as indicated in the figures, and top of the imaged object 2 where point 101 is located refers to this orientation. However, any other suitable orientation and position of the overall system is also possible. Also, an X-ray source 11 scan direction from left to right is shown in the figures for illustration only and all other suitable scan directions may also be used.

If the X-ray source 11 moves 240 microns during the X-ray shot while the detector 13 remains stationary, then the image of point 101 in object 2 shifts 40 microns (240 divided by a magnification of 6 equals 40) on the detector 13 from point 104 to point 105. The image of point 102 in object 2 shifts by a smaller amount on the detector 13 from point 106 to point 107, since point 102 is closer to the detector 13 than point 101. The image of point 103 in object 2 does not shift at all on the detector 13 because it is located right next to the detector. Thus, the maximum shift for a stationary detector 13 is 40 microns for X-ray source movement of 240 microns and a magnification of 6. The 40 micron shift leads to a blurring of an image of region 101 in a top portion of object 2. This blurring will be referred to as motion blurring due to the X-ray source and detector motion, in contrast to the vibration blurring due to X-ray source vibration from deceleration.

According to the second preferred aspect of the first preferred embodiment of the invention, the system 1 operates in the continuous mode, where the X-ray source 11 emits an X-ray beam 3 while the X-ray source is in motion in the first direction (i.e., to the right along path 4 in FIG. 1). At the same time, the detector 13 is translated in an opposite second direction (i.e., to the left along path 7 in FIG. 1) while the X-ray source 11 is emitting the X-ray beam 3. The detector motion reduces the amount of blurring in the continuous mode of operating the system 1.

Figure 5:
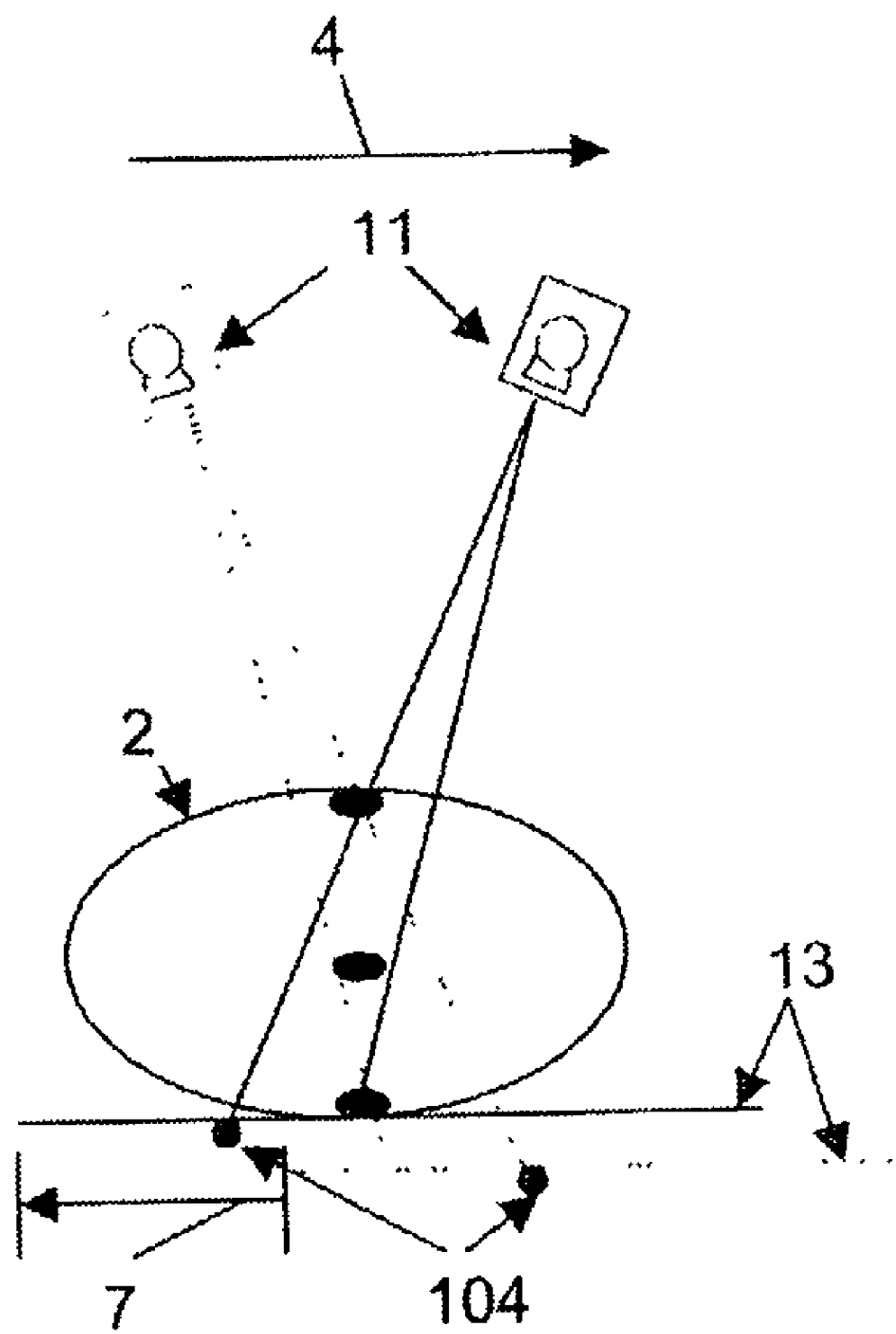

For example, FIG. 5 illustrates a case where the detector 13 is translated by 40 microns in the direction opposite to the direction of rotation of the X-ray source 11 along path 4. The X-ray source rotates by 240 microns along path 4 while emitting the X-ray beam 3. As shown in FIG. 5, the blurring of the image of point 101 in object 2 is about zero, because the X-ray beam 3 is always incident on the same spot 104 on the moving detector 13. The image of point 102 in the middle of the object 2 is blurred by the same amount as in FIG. 4, and image of point 103 at the bottom of object 2 is blurred by 40 microns due to the movement of the detector 13. Thus, the movement of the detector 13 in FIG. 5 is used to reduce the blurring in the top portion of the object 2, in case this is a critical area of the object that needs to be examined. However, the maximum blurring for the set up in FIG. 5 is still 40 microns.

Figure 6:
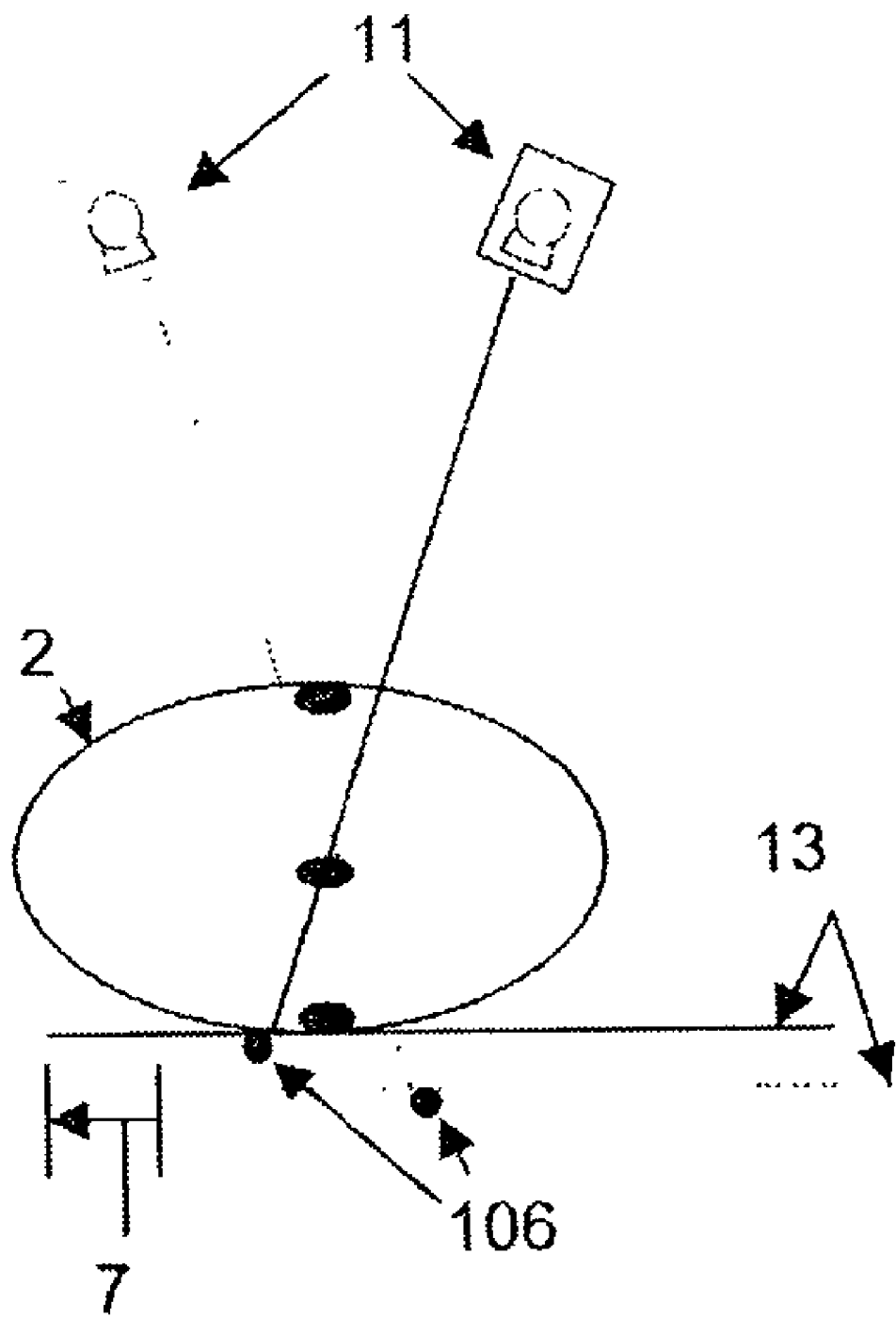

In order to reduce the maximum blurring amount, movement distance and speed during the X-ray shot are selected to minimize the maximum motion blurring amount. It is preferable to move the detector 13 and the X-ray source 11 in a manner which minimizes motion blurring in the middle of the object 2. Preferably, the detector 13 and the X-ray source 11 are moved at speeds and intervals which set blurring in the middle of the object to zero or as close to zero as possible. For example, as shown in FIG. 6, the detector 13 is translated 20 microns to the left while the X-ray source 11 is rotated 240 microns to the right. Thus, the blurring of image of point 102 is about zero because the X-ray beam passing through point 102 is incident on the same spot 106 on the moving detector 13. The maximum blurring of 20 microns occurs for images of points 101 and 103. Thus, the maximum blurring is reduced by 50% compared to the example of FIG. 4 where the detector is stationary.

The movement of the detector 13 in continuous mode of operation of the system provides about the same reduction in vibration blurring as continuous mode operation with a stationary detector 13, and an additional advantage of reducing motion blurring. Moving the detector 13 in the direction opposite to the X-ray source 11 during the shot makes the shift of points in the object on the detector less than if the detector is not moved during the X-ray shot. The worst case motion blurring is reduced by approximately a factor of two (compared to continuous mode with a stationary detector) with proper choice of X-ray source and detector motion parameters.

In one preferred aspect, the detector 13 is moved back to its starting position between each X-ray shot. Thus, the detector is translated back to its starting position of the first direction (i.e., to the right along path 7 in FIG. 1) while the X-ray source 11 does not emit the beam of X-rays 3 and the X-ray source 111 moves in the first direction. Thus, the detector moves in the same direction as the X-ray source between shots and in the opposite direction from the X-ray source during the shots. It should be noted that the detector 13 motion is not limited to a linear path motion, but may include any suitable motion described herein.

Preferably, the detector 13 is translated by 5 to 60 microns, such as by 20 to 40 microns. Preferably, the X-ray source 11 rotates through a path of 10 to 750 microns, such as 120 to 240 microns, during each shot. The preferred magnification (i.e., a ratio of source movement during a shot to image shift on the detector) is 1.05 to 8, such as 2 to 7. Preferably, each X-ray shot lasts about 150 to 350 milliseconds, such as about 200 to about 300 milliseconds. Preferably, the X-ray source 11 moves ten to one thousand times faster, such as one hundred to three hundred times faster, between the X-ray shots than during the X-ray shots. Other suitable motion parameters may be used instead.

In a preferred aspect, in order to implement the continuous mode of operation with a movable detector, a programmable controller for the actuator preferably moves the detector in a continuous back and forth motion at a constant velocity. Preferably, the motion of the detector 13 is initiated with an X-ray synchronization signal to move the detector during the X-ray shot.

If desired, the methods of the first and second preferred aspects of the first embodiment may be combined. In this method, the detector 13 does not move back all the way to its starting position between X-ray shots, but moves part of the way back to its starting position between shots. During a subsequent shot, the detector moves further in the second direction (i.e., to the left) than during a previous shot. This allows the detector to face the X-ray source 11 in any X-ray source position, such that the detector is always essentially opposite of the X-ray source, relative to the imaged object. In another preferred aspect, the detector moves only in the second direction (i.e., to the left), with the detector position at the start of the shot, and the detector movement during the shot, adapted to the X-ray source position at the start of the shot, and the X-ray source movement during the shot. If desired, the detector 13 may move at a first speed during the shot and at a different second speed, such as at a greater speed between the shots.

In a third preferred aspect of the first embodiment, the detector 13 is rotated inside the housing 14 in the y-direction, as shown by path 8 in FIGS. 1 and 2. In other words, the detector 13 rotates such that its upper surface tilts at a given angle with respect to the X-ray source rotation plane. Thus, in the third preferred aspect, the X-ray source 11 moves the X-ray beam 3 in the y-direction outside the X-ray source 11 rotation plane, as will be discussed in more detail with respect to the second preferred embodiment. As the X-ray beam 3 moves in the y-direction, the detector 13 rotates in the y-direction at the same time, as shown by arrows 8 in FIGS. 1 and 2. One advantage of this rotation is to keep the upper detector surface perpendicular to the incident X-ray beam 3 when the X-ray beam 3 is moved in the y-direction. Preferably, a relatively small rotation of detector is implemented. The tilt of the detector 13 can be in any suitable direction in addition to or instead of direction of path 8, such that the incoming X-rays are maintained as close as possible to being perpendicular to the detector surface. In particular, while the X-ray source travels along the rotational path in a sector, the detector may tilt in the same angular direction, such that the incoming X-rays are maintained as close as possible to being perpendicular to the detector surface. If desired, the detector 13 may be tilted in combination with the translation of the detector along path 7, where the translation is within a plane or outside a plane, as discussed with respect the fourth preferred aspect below.

In a fourth preferred aspect of the first embodiment, an optional curved breast support plate is provided over the detector 13 for mammography tomosynthesis. In this aspect, the detector 13 rotates at the same time with the X-ray source 11 over the scanning angular range. Thus, the detector 13 moves in an arc shaped path 9 in a direction (i.e., the left along path 9 shown in FIG. 1) opposite to the rotation direction of the X-ray source (i.e., to the right along path 4 in FIG. 1). Preferably, the optional, curved, X-ray transparent breast support plate is provided to allow the detector 13 to rotate below the support plate. If desired, the housing 14 may also rotate with the detector 13. This rotation configuration is similar to a CT rotation configuration. One advantage of this rotation is to keep the upper detector surface perpendicular to the X-ray beam. In another preferred aspect, the angular range for the detector 13 movement may be smaller than the angular range for the X-ray source 11 movement. Thus, the detector 13 sweeps through the full angular range as the source 111 sweeps through the full angular range, in respective opposite directions, where the detector may be controlled according to one or more aspects of the present invention.

It should be noted that the detector 13 may also be moved in any combination of directions described with respect to the first through fourth preferred aspects above. Thus, during the rotation of the X-ray source 11 along path 4, the detector 13 may move along any two of or in all three of the paths 7, 8 and 9. This combined path is a complex non-linear path.

In a second preferred embodiment of the present invention, the X-ray source 11 irradiates the object 2 with the beam of X-rays 3 such that a focal point of the beam of X-rays follows a non arc shaped path relative to the detector 13. The preferred aspects of the second embodiment are described below.

In a first preferred aspect of the second embodiment, the X-ray source 11 rotates in a first angular direction along the rotational path 4 and the focal point of the X-ray beam moves along with the X-ray source and also moves in a second direction substantially along the redirection (i.e., the radial direction), as shown by path 5 in FIGS. 1 and 2. The X-ray beam focal point may be moved in the r-direction by moving the X-ray source in the r-direction along path 5, by changing the position of an electron beam focal spot on an X-ray target located in the X-ray tube located in the X-ray source 11 and/or by using an X-ray lens.

For example, the X-ray source 11 may be mechanically or piezoelectrically shifted in the redirection, depending on the desired magnitude of the shift. A piezoelectric actuator may be used to piezoelectrically move the X-ray source. A ball screw or another mechanical actuator may be used to mechanically move the X-ray source 11 in the r-direction. If the X-ray source 11 is mounted on rotating arm 27 shown in FIG. 2, then the arm 27 may contain a track to allow redirection movement of the X-ray source 11. Alternatively, a movable arm or a movable plate driven by a motor or any other suitable motion imparting device may be used to mechanically move the X-ray source 11 in the redirection. If desired, the X-ray source 11 may be moved along the r direction by different amounts for different angular positions. Thus, in one embodiment, the source 11 effectively moves along a line at a fixed height above the detector. This geometry simplifies certain aspects of the image reconstruction. Therefore, a three dimensional image of the object 2 may be formed from a substantially linear motion of the X-ray source 11.

The shifting of the electron beam focal spot on the X-ray target in the X-ray tube can be used to move the X-ray beam 3 focal spot in the redirection. The shifting of the electron beam focal spot may be accomplished by electronically steering the electron beam to a different spot on the X-ray target or by using an X-ray tube with one or more electron beam sources and distributed focal spots on one or more X-ray targets. To shift the X-ray beam 3 focal spot, a first electron beam aimed at a first spot on the first X-ray target is turned off and a second electron beam aimed at different second spot on the first or second X-ray target is turned on. Since the electron beam strikes a different spot on the X-ray target, the X-ray beam will be emitted from a different spot on the target, thus shifting the position of the X-ray beam focal spot. If desired, the X-ray target may be specially positioned in the X-ray tube to allow easy shifting of the X-ray beam focal spot.

A fiberoptic X-ray lens may also be used to shift the X-ray beam focal spot in the r direction. The X-ray beam 3 focal spot may be shifted by passing the beam through different fiberoptic strands of the bundle. Since the strands are directed toward slightly different directions, passing the X-ray beam through different strands shifts the beam focal spot in the desired direction. A shutter may be used to steer the beam 3 into a particular strand or group of strands. Fiberoptic X-ray lenses are available from X-ray Optical Systems Inc. of Albany, N.Y. and other sources. A combination of two or more methods to shift the focal spot of the X-ray beam in the redirection may also be used, if desired.

In a second preferred aspect of the second preferred embodiment, the X-ray beam 3 focal spot is shifted in the y-direction along path 6 shown in FIGS. 2 and 3. One benefit of beam focal spot motion in the y-direction is that it allows the tomosynthesis focusing process to work in both directions in the reconstructed planes, and not just in one. Furthermore, y-direction motion improves depth resolution during imaging. Thus, the X-ray source 11 rotates in a first angular direction along path 4 and the X-ray beam 3 focal spot moves in third and fourth directions (i.e., back and forth in the y-direction) along path 6 outside a plane of rotation 4 of the X-ray source, as shown in FIG. 3. In another embodiment, the focal spot of the X-ray beam moves only in the third, or only in the fourth direction.

The X-ray beam 3 focal spot may be moved in the y-direction by moving (i.e. translating and/or rotating) the X-ray source 111 in the y-direction along path 6, by changing the position of an electron beam focal spot on an X-ray target located in the X-ray tube located in the X-ray source 11 and/or by using the X-ray lens to shift the X-ray beam 3 in the y-direction. A combination of two or more of these methods may also be used if desired. As in the first preferred aspect of the second embodiment, piezoelectric or mechanical actuators may be used to move the X-ray source 11 in the y-direction. Electron beam shifting or plural electron beams may be used to shift the X-ray focal spot in the y-direction.

Figure 7:
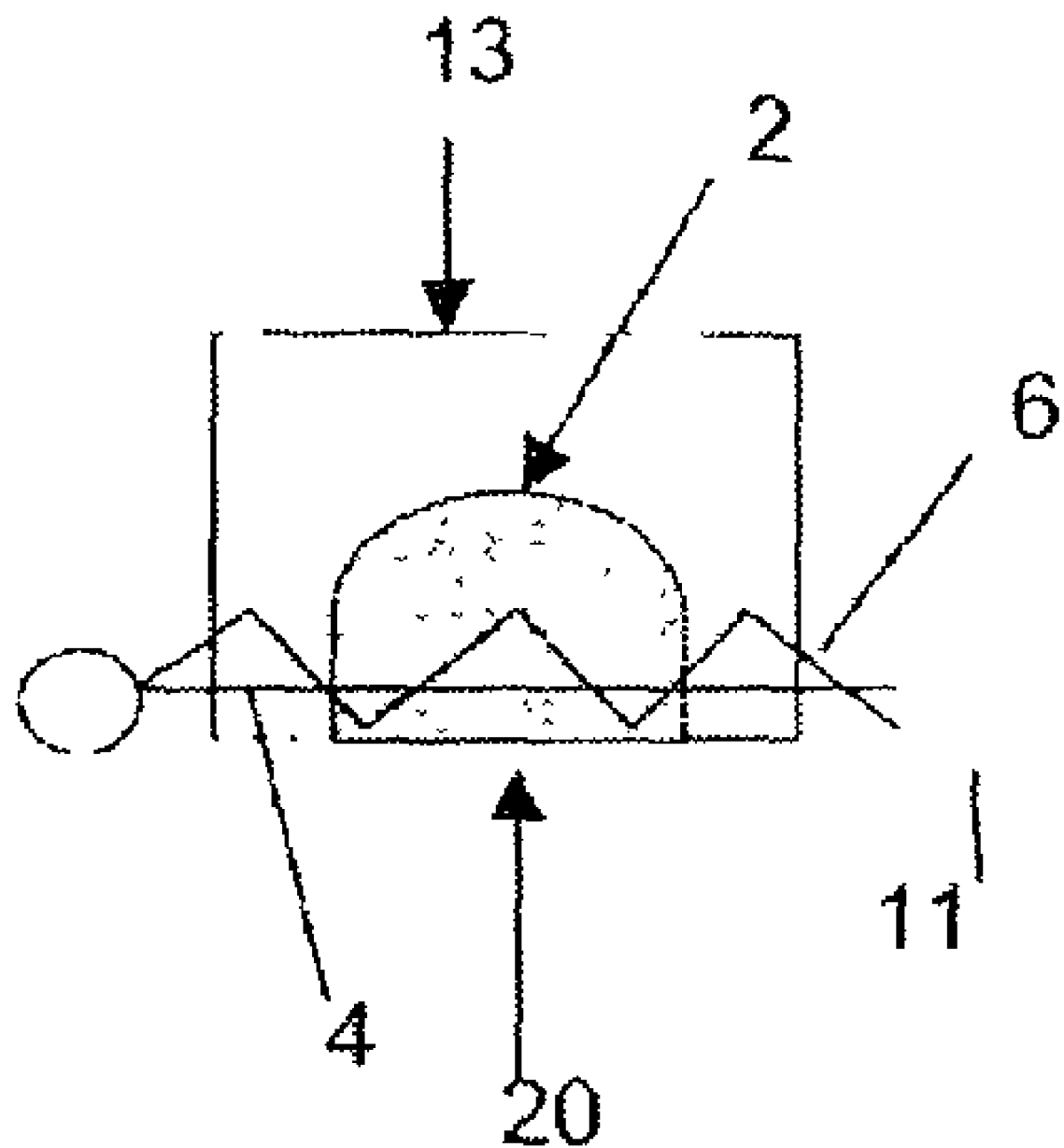
FIG. 7 is schematic top view illustration of the system according to a preferred embodiment of the invention.

FIG. 7 illustrates a top view of the system 1 showing the path 6 of the X-ray beam 3 focal spot. The path 6 may have any suitable shape, as shown in FIG. 7. For example, the path 6 may have a saw tooth shape which deviates from the arc shaped path 4 (shown as a line from the top view) toward and away from the patient chest wall 20. Preferably, the X-ray beam 3 shots are emitted at the vertices of the saw tooth shaped path 6 (i.e., at the tips or points of maximum deviation from path 4). However, the X-ray beam 3 shots may be emitted at any desired point on the path 6. Furthermore, if the system 1 operates in the continuous rather than in the step and shoot mode, then the X-ray beam 3 is continuously emitted from a plurality of intervals of contiguous points on path 6. While path 6 has a saw tooth shape in FIG. 7, the path may have any desired shape. For example, the path 6 may have a square wave, a sinusoidal wave (i.e., sine wave) or a trapezoidal wave (i.e., inclined lines when moving toward or away from the chest wall 20 separated by lines parallel to the chest wall 20) shape. Alternatively, the complete path 6 may comprise two or more segments, where the X-ray source 11 moves in one direction (such as left to right) in the plane of rotation, then moves in the y-direction, and then moves in the opposite direction (such as right to left) in the plane of rotation.

In a third preferred embodiment of the invention, the center of the X-ray beam 3 is aligned with the center of the detector 13. This alignment is important if the X-ray source 111 rotation axis 12 is located far from the upper surface of the detector. The center of the X-ray beam 3 is preferably aligned with the center of the detector 13 by turning the X-ray source in direction 10 shown in FIG. 1 or by collimating the beam to select the region that falls on the surface of the detector. The X-ray source 111 is preferably mechanically turned in direction 10, such as by mounting the X-ray source on a mounting bracket with one degree of freedom and then rotating the X-ray source on this bracket. Other suitable rotational mechanisms and methods may also be used. This way, the center of the X-ray beam 3 impinges substantially on the same location (i.e., within a several pixels, such as within 1 to 3 pixels) on the detector 13 from different positions along the rotational path 4 of the X-ray source. In another preferred aspect, the X-ray 11 source can be rotated on a mounting bracket with two degrees of freedom. This is particularly advantageous in the case where the X-ray source 11 is also moved in the y-direction along path 6.

Figure 8:
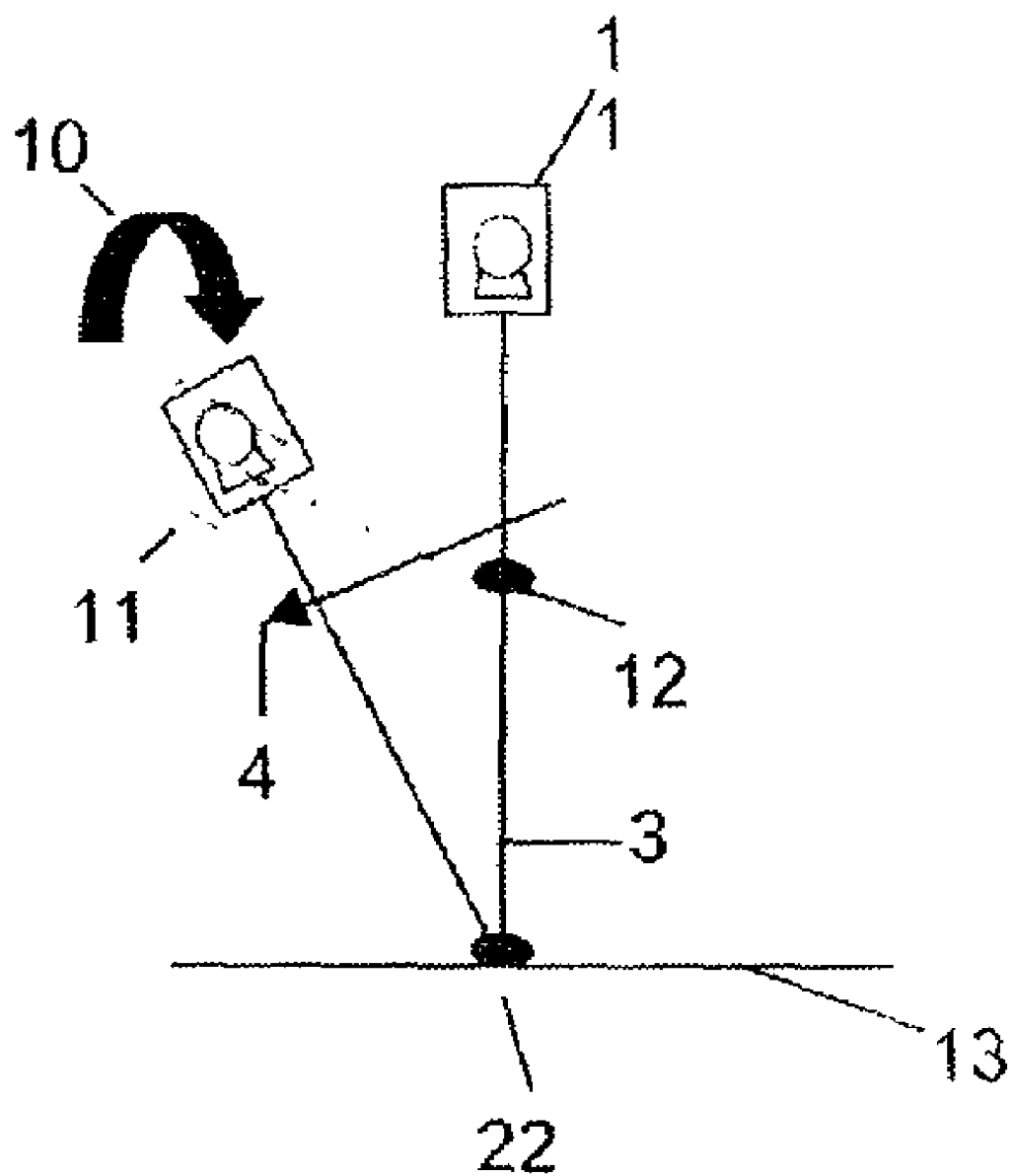

For example, FIG. 8 illustrates a system 1 where the rotation axis 12 is located far from the upper surface of the detector 13. When the X-ray source 11 is positioned in a first position, directly over location 22 on the detector 13, the X-ray beam 3 impinges directly on location 22. However, as the X-ray source 11 is rotated along path 4 (right to left as shown in FIG. 8), if the X-ray source 11 is not rotated in direction 10 (the unrotated X-ray source 11 is shown in dashed lines), then the hypothetical X-ray beam 3 (shown by the dashed line) would pass through the rotation axis 12 and would miss the detector 13 (as well as the object being imaged) or it would impinge on a different location on the detector than location 22. This would cause the image to be incomplete or blurred. However, by turning the X-ray source 11 in the direction 10, when the X-ray source 11 is in a second position (to the left in FIG. 8), then the central ray of the X-ray beam 3 (solid line in FIG. 8) impinges on substantially the same location 22 on the detector.

The X-ray source 11 is preferably turned such that the central ray of the beam falls onto the center of the detector, for example in direction 10, between each shot or between every other shot. The X-ray source 11 may be turned while it is moving along path 4 or during stops along path 4. A similar result may be achieved by using a collimator to select the region of the beam that falls on the detector surface.

It should be noted that the X-ray beam focal spot may also be moved in any combination of directions described with respect to the second and third preferred embodiments above. Thus, during the rotation of the X-ray source 11 along path 4, the focal spot of X-ray beam 3 may move in any two of or in all three of the r-direction 5, in the y-direction 6 and in direction 10. The focal spot of X-ray beam 3 may move in redirection 5, in the y-direction 6 and in direction 10 due to any combination of movement of the X-ray source 11, the shifting of the electron beam on the X-ray target or the use of an X-ray lens. This combined path is a complex nonlinear path. Furthermore, if desired, the size of the electron beam focal spot on the X-ray target may be changed to change the size and/or the position of the X-ray beam emitted from the target.

In a fourth preferred embodiment of the present invention, the detector 13 moves relative to the object 2 and the beam of X-rays 3 moves in a non arc shaped path relative to the detector 13. Thus, the fourth preferred embodiment combines the detector motion of the first preferred embodiment with the X-ray beam focal spot motion of the second preferred embodiment. Any suitable combination of the above described combinations of motion of the X-ray beam and the detector may be used together. In addition, each of the focal spot of the X-ray beam and the detector may move in two or more directions, as described with respect to the first and second preferred embodiments. If desired, the center of the X-ray beam 3 is aligned with the center of the detector 13 according to the third preferred embodiment in addition to the motion of the first and/or second embodiment.

In a fifth preferred embodiment of the present invention, two or more X-ray sources are used. In a first preferred aspect of the fifth embodiment, at least two X-ray sources 11, 111 rotate in respective arc shaped paths 4, 104. In one embodiment, the paths 4, 104 in their respective parallel planes are offset from each other in the y-direction 6 (i.e., in a direction perpendicular to the rotation planes), as shown in FIGS. 2 and 3. The sources 11, 111 may rotate in the same direction or in opposite directions along paths 4, 104. Thus, second X-ray source 111 rotates in a plane farther from the patient chest wall 20 than the first X-ray source 11. If the sources 11, 111 rotate in the same direction, then preferably, the first X-ray source 11 is also offset from the second X-ray source 111 in the rotation direction (i.e., along path 4) during rotation in the arc shaped path. The second X-ray source 111 also moves ahead or behind the first X-ray source 111 along its rotation path 104, as shown in FIG. 3. Preferably, the motion is controlled such as to minimize system vibration and motion blurring, and to optimize the geometric distribution of source positions during the X-ray shots. To minimize system vibration, it may be beneficial to move sources 11, 111 in substantially opposite directions.

One advantage of using two or more X-rays sources offset in the y-direction is the ability to image the imaged object 2 from different y-orientations. This results in an improved depth resolution. One advantage of offsetting the X-ray sources 11, 111 in the rotation direction (i.e., along paths 4 and 104) is the increased speed of scanning and image formation. In the first preferred aspect of the fifth embodiment, the X-ray sources 11, 111 are turned on sequentially, such that one source is turned off and moving to its next position while the other source in emitting a shot and is moving slowly or remaining stationary during the shot. The X-ray sources 11, 111 preferably emit X-ray shots from different locations along the rotational paths 4, 104 to speed up the timing of the imaging, where both X-ray sources 11, 111 complete the entire path 4, 104.

In a second aspect of the fifth embodiment, each source 11, 111 completes a half of the scan to shorten the imaging time. In this aspect, the first source 11 completes the left side of path 4 while the second source 111 completes the right side of the path 104. The combined path of both sources 11, 111 results in a single arc shaped path. If three or more X-ray sources are used, then the paths and the imaging time can be shortened even further.

In a third preferred aspect of the fifth embodiment, the system 1 contains at least four stationary X-ray sources 11 which are adapted to sequentially irradiate the object 2 with the X-ray beams 3. The X-ray sources 11 are preferably spread out along one arc shaped path 4. If desired, the X-ray sources 11 may also be offset from each other in the r-direction 5 and/or in y-direction 6. Preferably 5 to 11 stationary X-ray sources are used. The advantage of stationary X-ray sources is the elimination of vibration blurring of the image, and a potentially shorter time to acquire the tomosynthesis projections.

The X-ray sources sequentially irradiate the object 2 by being turned on sequentially. Alternatively, all the sources may be turned on all the time, and a shutter may be used to close off the beam on all but the one of the sources at any given time. It should be noted that in the fifth preferred embodiment, the detector 13 may be stationary or be moved in the directions described in the first preferred embodiment. Furthermore, the motion of the second through fourth embodiments may also be added.

Figure 9:
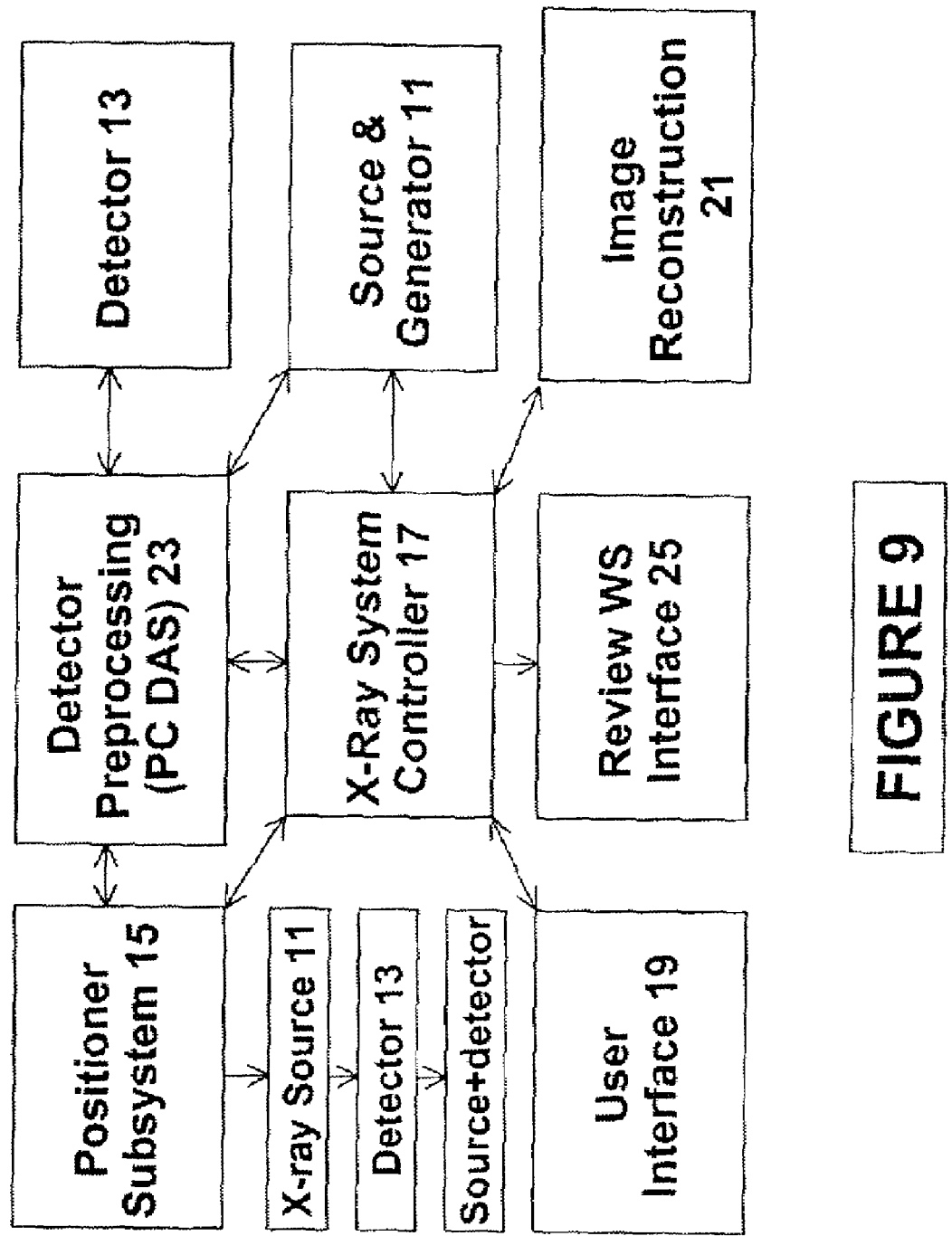
FIG. 9 is a block diagram of system components according to the preferred embodiments of the invention.

FIG. 9 is an illustration of the preferred components of an X-ray mammography tomosynthesis system 1 according to the preferred embodiments of the present invention. It should be noted that the system 1 may have additional components or lack one or more of the components described below. The system contains an X-ray source 11, such as an X-ray tube, generator and housing, and a detector 13, such as a digital detector. A positioner subsystem 15, such as a motor controller and/or a piezoelectric actuator, is used to position the X-ray source 11 and/or the detector 13.

The X-ray system 1 also contains various electronic components. These components may comprise a single special or general purpose computer or a microprocessor chip, such as an ASIC chip. Alternatively, these electronic components may comprise several connected computers, processors or work stations. FIG. 9 illustrates how all of these components are interconnected. The electronic components include the X-ray system controller 17, which controls the other electronic components, the positioner subsystem 15 and the X-ray source 11. The system 1 also contains a user interface 19 and an image reconstruction section 21 which reconstructs a three dimensional image from two dimensional projection radiographs. A detector preprocessing and prefiltering section 23, such as a PC data acquisition subsystem, is connected to the detector 13. This section 23 removes artifacts, provides thickness compensation and data segmentation for the X-ray system 1.

Preferably, during and/or after acquiring a set of tomosynthesis projections, the three dimensional image is reconstructed using a reconstruction method that directly accounts for the system geometry rather than transforming the image of each two dimensional projection image to an image based on the Twinning principle, and then using the shift and add reconstruction method, as described in prior art U.S. Pat. No. 5,872,828. This allows for example the detector 13 to move during imaging while generating a three dimensional volumetric image of the object 2. One back-projection reconstruction method is disclosed in related U.S. patent application Ser. No. 10/063,356, to Jeffrey Eberhard and Bernhard Claus titled "Generalized Filtered Back-Projection Reconstruction In Digital Tomosynthesis" filed on Apr. 15, 2002 and incorporated herein by reference in its entirety. Other reconstruction methods may also be used if desired. However, while less preferred, the reconstruction method described U.S. Pat. No. 5,872,828 may also be used in embodiments where the detector is stationary.

The X-ray system 1 also contains an optional review work station interface 25. This interface 25 is used to present to a clinician certain quantitative metrics extracted from the image. The clinician selects one or more metrics from a set of metrics to be computed and displayed on a workstation display or screen, whereby the metrics are displayed along with a mammographic image. For instance, interface 25 may be used to provide to the clinician access to 1) the overall percent glandular composition or 2) the percentage glandular distribution. Further, after delineation of findings (microcalcifications, masses, or vessels, e.g.), either via computer-aided diagnosis (CAD) algorithms or by hand-labeling, it may provide a summary of the quantitative measures of the findings. Such a preferred interface is disclosed in related U.S. patent application Ser. No. 10/063,353, John Kaufhold, Bernhard Claus and Jeffrey Eberhard titled "Method And Apparatus For Providing Mammographic Image Metrics To A Clinician" filed on Apr. 14, 2002 and incorporated herein by reference in its entirety.

Figure 10:
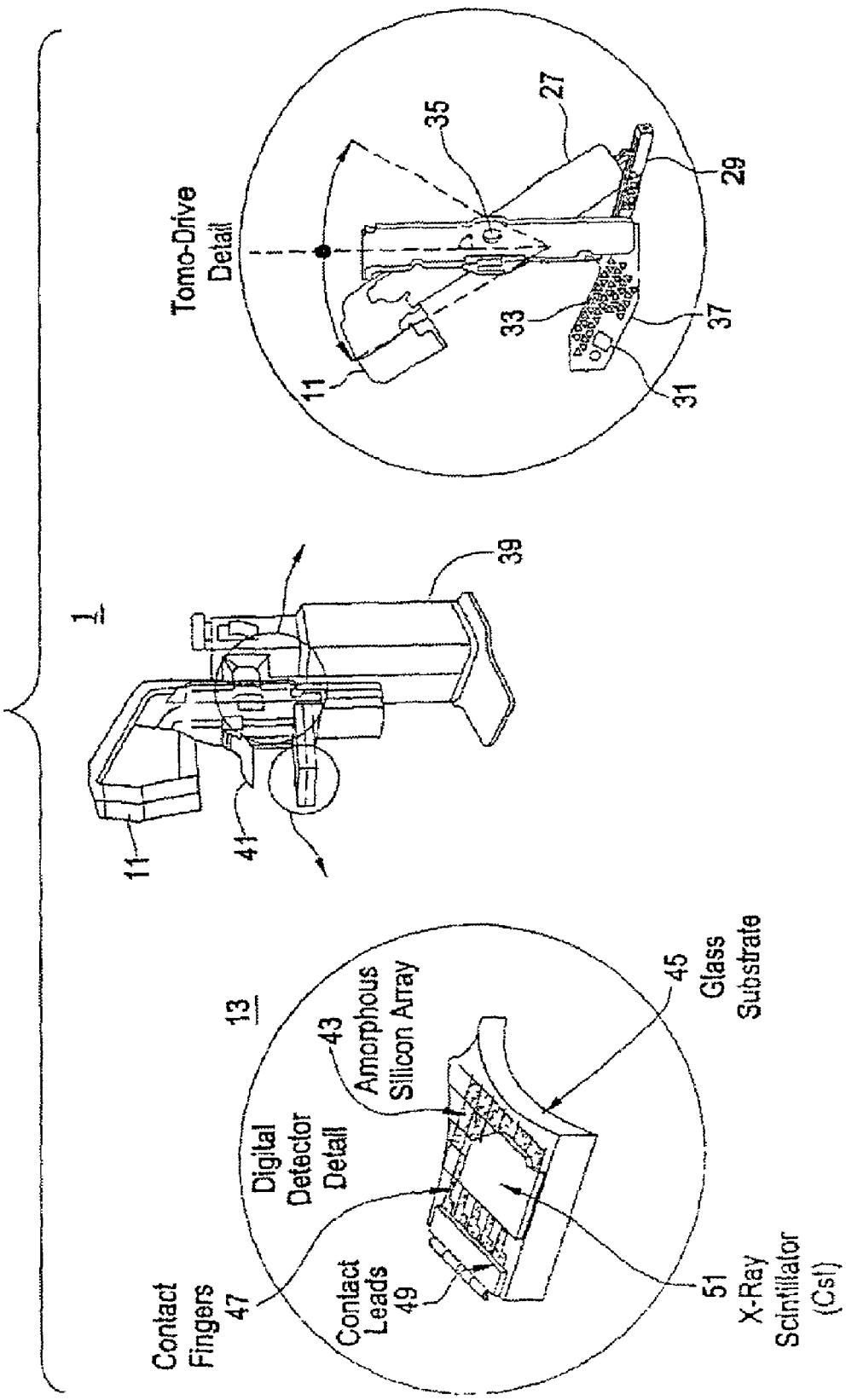
FIG. 10 is a three dimensional view of a system according to the preferred embodiments of the invention.

The X-ray tomosynthesis system 1 may have any desired physical layout which provides multiple projection radiographs of the imaged breast from a pass of the X-ray source through the predefined trajectory, from which a 3D representation of the imaged breast is reconstructed in the image reconstruction section 21. FIG. 10 illustrates one layout of the X-ray tomosynthesis system 1 with a track for moving the X-ray source. This system is described in detail in related U.S. patent application Ser. No. 10/063,357, to Yu Wang, Reinhold Wirth and James Alexander titled "Tomosynthesis X-ray Mammogram System And Method With Automatic Drive System" filed on Apr. 15, 2002 and incorporated herein by reference in its entirety.

The X-ray source 11 is mounted to an upper or first portion of the first arm 27. The first arm 27 may have any desired shape, such as a tube or plate shape. A lower or second portion of the first arm 27 distal from the first portion is mounted to a linear motion track 29.

The mechanical driving mechanism, such as a ball screw driven by a motor (not shown in the figure because the ball screw is located in the track) is adapted to move the lower portion of the first arm 27 along the track 29, to move the X-ray source 11 in the arc shaped path. The motor may also be mounted onto the track if desired. A side pin 31 is positioned to create a stable whole range drive by allowing the track 29 to rotate with respect to a fixed point.

The detector 13 is mounted to a second support or arm 33. Typical detector size for X-ray acquisition is 24 cm×30 cm or 18 cm×24 cm. However, other suitable dimensions may be used. The second arm 33 may have any desired shape, such as a tube or plate shape. A shaft 35 connects the middle portions of the first arm 27 and the second arm 33, such that the arms 27, 33 may rotate relative to each other about the shaft 35 in a scissors-like motion. Preferably, the second arm 33 is stationary while the first arm 27 rotates.

In a preferred aspect of the first embodiment, a pivot point plate 37 is attached to the second arm 33, as shown in FIG. 10. The pivot point plate 37 is rotatably mounted to the linear motion track 29 by the side pin 31. The pivot plate 37 and track 29 optionally have holes which reduce the weight of the plate and track. If desired, the second arm 33 supporting the detector 13 and the pivot plate 37 may remain stationary, while the first arm 27 rotates and the track 29 moves in a vertical plane with respect to the second arm 33 about the side pin 31. The combined motion of the first arm 27 and the track 29 allows the first arm to move along a linear motion track 29 while moving the X-ray source 11 in an arc shaped path. If desired, the X-ray source 11 may also be moved in the redirection and/or the y-direction as described above. If desired, the detector 13 may be moved in any direction described in the first preferred embodiment.

The X-ray source 11, detector 13 and associated supports and drives are mounted to a gantry or base 39. The detector 13 is mounted over the gantry 39 in a position which allows a patient to place her breast onto the detector. The system 1 may be adjustable in the vertical direction relative to the ground to allow patients of different height to use the system without stretching or bending. A breast compression paddle 41 is likewise height adjustable.

The preferred electronic detector 13 contains an amorphous silicon photodetector array 43 formed on a glass substrate 45. The array 43 includes metal contact fingers 47 and metal contact leads 49. An X-ray sensitive scintillator material 51, such as cesium iodide, is formed over the array 43. The scintillator material 51 emits radiation having a wavelength detectable by the silicon pixels in the array 43 in response to receiving an X-ray. However, various other solid state and vacuum digital X-ray detectors may be used instead. The magnitude of the radiation is a function of the attenuation of the X-rays by the imaged object 2. The pixels of array 43 convert the received radiation into an electrical signal of a maximum magnitude that is provided to the preprocessor 23 and then converted into an image.

Figure 11:
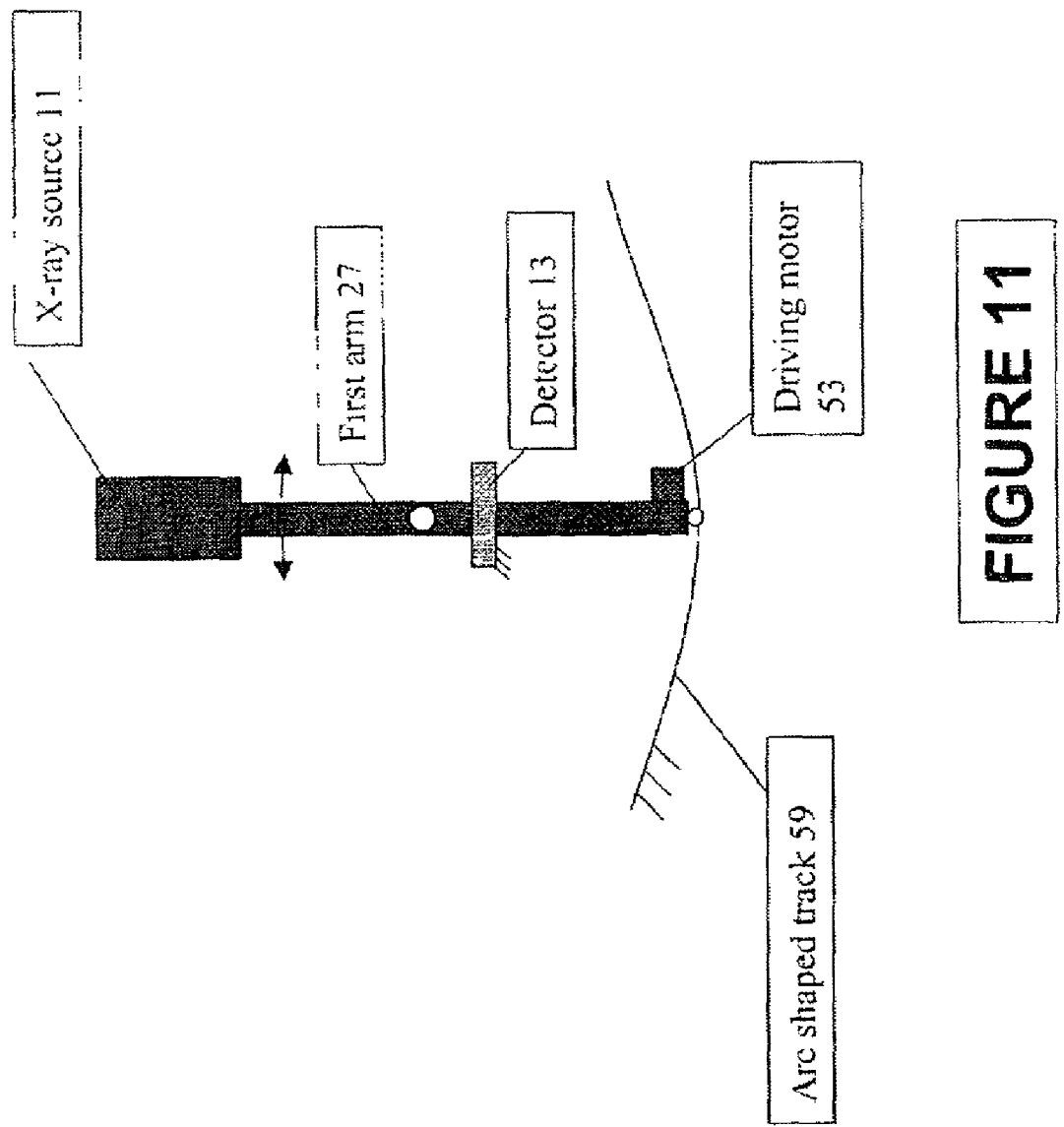

However, in alternative preferred aspects of the X-ray tomosynthesis system 1, an arc shaped track is used instead of a linear motion track. For example, in a second preferred aspect, an arc shaped track 59 is used instead of a linear motion track 29, as schematically illustrated in FIG. 11. The lower portion of the first arm 27 is moved along the track 59 by a motor 53. This causes the X-ray source 11 supported by the upper portion of the first arm 27 to move in an arc shaped path.

Figure 12:
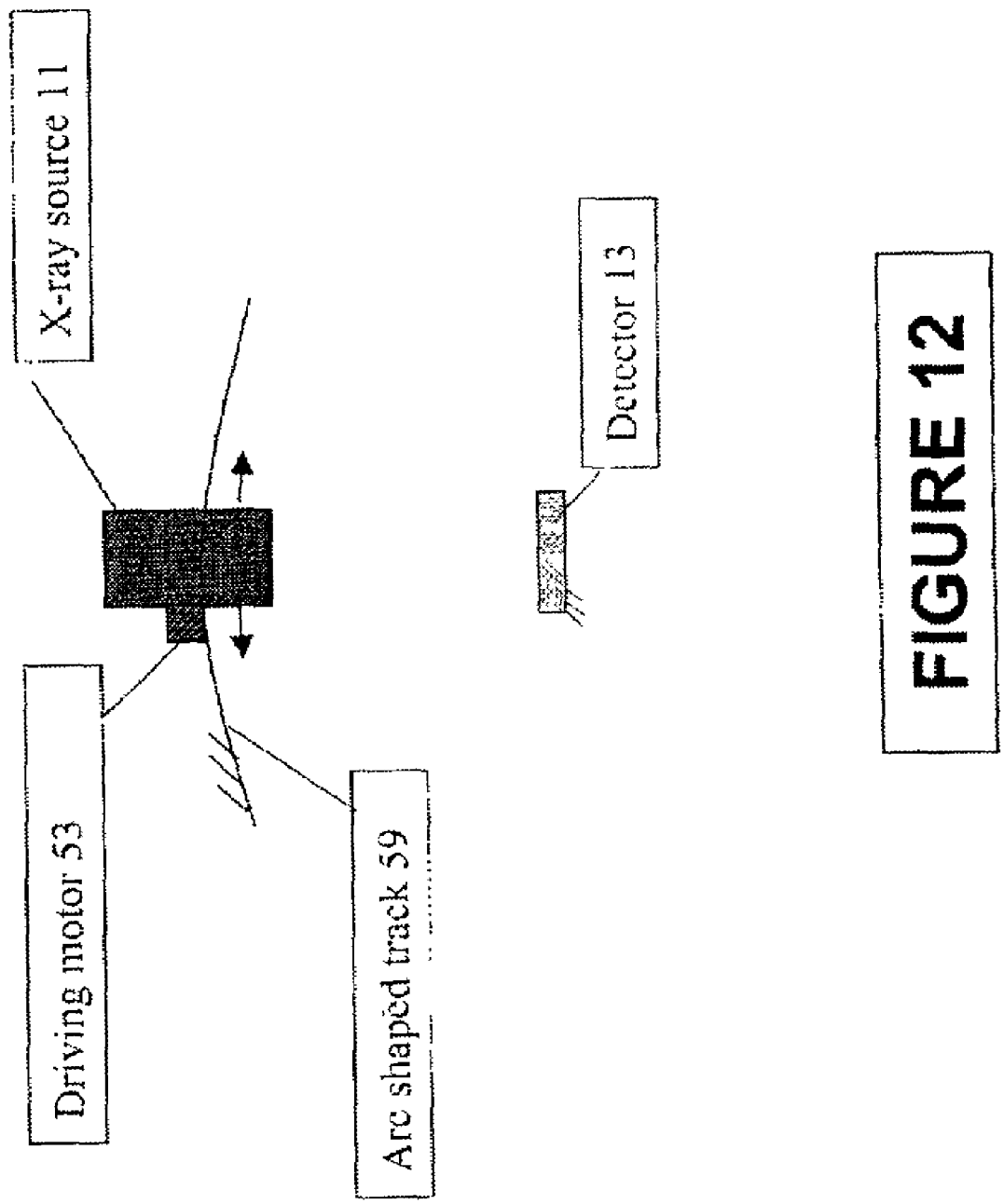

The system 1 of the third preferred aspect is schematically illustrated in FIG. 12. In this embodiment, the X-ray source 111 is mounted directly to the arc shaped track 59. The motor 53 is attached to the X-ray source 11 and is adapted to move the X-ray source along the arc shaped track 59. The motor 53 is also preferably attached to the track 59. The digital detector 13 is located facing the X-ray source 11 such that an imaging area is formed above the detector. In this embodiment, the first arm 27 may be omitted.

Figure 13:
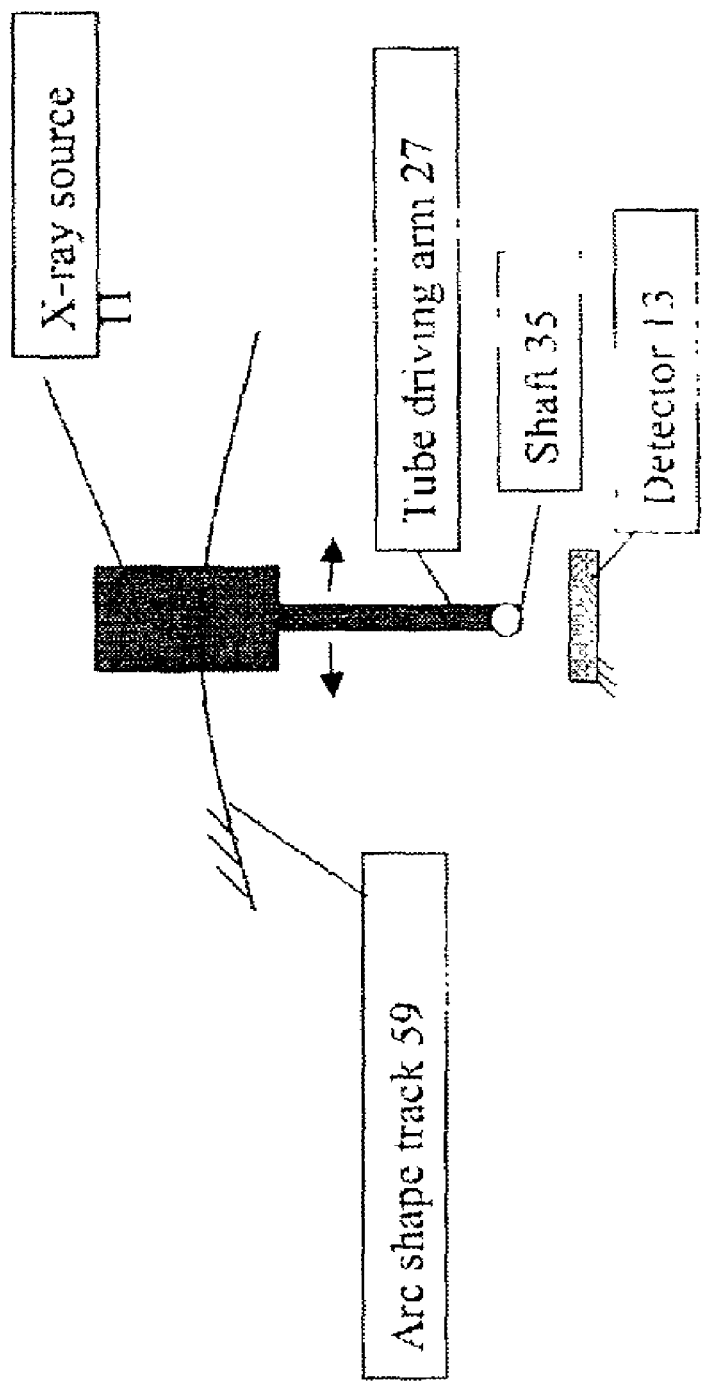

The system 1 of the fourth preferred aspect is schematically illustrated in FIG. 13. In this embodiment, the X-ray source 111 is also mounted to the arc shaped track 59. However, the first arm 27 is used to move the X-ray source 11 in the arc shaped path. Preferably, the first arm 27 is made relatively thin and light weight to minimize its mass, but has sufficient rigidity to move the X-ray source 11 along the track 59. The first arm 27 connects the X-ray source 11 to the shaft 35. The shaft 35 connects the first arm 27 to the second arm 33 supporting the detector 13. The shaft 35 is turned by a motor or other rotation imparting device (not shown). The step motion of the X-ray source 11 is produced from the shaft 35 torque through the first arm 27. Since a track is used to move the X-ray source 11 in the four above described aspects, the X-ray source 11 motion is precisely controlled by the track. This reduces the system vibration and improves the image quality. In another embodiment, the track in the above described aspects of the present invention is non arc shaped.

The system 1 of the fifth preferred aspect is schematically illustrated in FIG. 14. The detector 13 is mounted on a stationary portion of the gantry 39. The X-ray source 11 is mounted onto an upper portion of a movable arm 27. The lower end of the arm 27 is pivotably attached to the gantry 39. As shown in FIG. 7, the X-ray source 11 pivots from arm 27 about a point 35 (such as a shaft) above the detector 13. The X-ray source 11 is stationary or moving during the exposure and then is moved to the next position in its path before obtaining the next image. An actuator or control mechanism 53, such as a motor, is used to rotate the arm 27 around shaft 35. The detector 13 may be stationary or moving during the process. The X-ray source 11 and the detector 13 may move in any suitable path described herein.

While the figures illustrate an upright mammography system, the present invention is not limited to this configuration. For example the system may have a prone table layout where the patient lies down during imaging, or any other suitable layout.

The preferred embodiments have been set forth herein for the purpose of illustration. However, this description should not be deemed to be a limitation on the scope of the invention. Accordingly, various modifications, adaptations, and alternatives may occur to one skilled in the art without departing from the scope of the claimed inventive concept.

What is claimed is:

1. A tomosynthesis system for forming a three dimensional image of an object, comprising:
    an X-ray source configured to irradiate the object with a beam of X-rays from a plurality of positions along a path in a sector;
    an X-ray detector positioned relative to the X-ray source to detect X-rays transmitted through the object; and
    a processor which is configured to generate a three dimensional image of the object based on X-rays detected by the detector;
    wherein:
    the X-ray source irradiates the object with the beam of X-rays such that the focal spot of the beam of X-rays follows a non arc shaped path; or
    a center of the beam of X-rays impinges substantially on the same location on the detector from different X-ray source positions in the sector.

2. The system of claim 1, wherein the system comprises a mammography tomosynthesis system and the object comprises a human breast.

3. The system of claim 2, wherein the detector is adapted to move relative to the object.

4. The system of 3, further comprising:
    a detector housing; and
    a piezoelectric actuator configured to move the detector in the detector housing.

5. The system of claim 3, wherein:
    the X-ray source is configured to rotate in an arc shaped path in a first direction relative to the object; and
    the detector is configured to move in a path in a plane in a second direction opposite to the first direction during rotation of the X-ray source.

6. The system of claim 3, wherein:
    the X-ray source is configured to rotate along the path in the sector in a first angular direction relative to the object, such that the focal spot of the X-ray beam moves in the first angular direction; and
    the detector is configured to rotate in the direction different from the first angular direction.

7. The system of claim 3, wherein:
    the X-ray source is configured to rotate in an arc shaped path in a first angular direction relative to the object; and
    the detector is configured to move in an arc shaped path in a second angular direction opposite to the first direction.

8. The system of claim 2, wherein the X-ray source is configured to irradiate the object with the beam of X-rays such that the focal spot of the beam of X-rays follows a non arc shaped path relative to the detector.

9. The system of claim 8, wherein the X-ray source is configured to rotate in a first angular direction along the path and to move in a second direction substantially along a second radial direction.

10. The system of claim 8, wherein the X-ray source is configured to rotate in a first angular direction and an electron beam focal spot is adapted to change position on an X-ray target in the X-ray source to move the X-ray beam focal spot in a second direction substantially along the second radial direction.

11. The system of claim 8, wherein the X-ray source is configured to rotate along the path in a first angular direction and move in at least one of a third and fourth directions outside a plane of rotation of the X-ray source.

12. The system of claim 8, wherein the X-ray source is configured to rotate along the path in a first angular direction and an electron beam focal spot is configured to change position on an X-ray target in the X-ray source to move the X-ray beam focal spot in at least one of a third and fourth directions outside a plane of rotation of the X-ray source.

13. The system of claim 8, wherein the X-ray source is configured to rotate along the path in a first angular direction and an X-ray lens is adapted move the X-ray beam focal spot in at least one of a third and fourth directions outside a plane of rotation of the X-ray source.

14. The system of claim 2, wherein the X-ray source is configured to rotate along the path in a first angular direction and to turn in a fifth direction such that the center of the X-ray beam impinges substantially on the same location on the detector from different X-ray source positions in the sector.

15. The system of claim 2, wherein the X-ray source is configured to rotate along the path in a first angular direction and a collimator changes a position of the X-ray beam to turn the X-ray beam in a fifth direction such that the center of the X-ray beam impinges substantially on the same location on the detector from different X-ray source positions in the sector.

16. The system of claim 2, wherein:
    the detector is configured to move relative to the object; and
    the X-ray source is configured to irradiate the object with the beam of X-rays such that the focal spot of the beam of X-rays follows a non arc shaped path relative to the detector.

17. A tomosynthesis system for forming a three dimensional image of an object, comprising:
    a first means for irradiating the object with a beam of X-rays from a plurality of positions along a path in a sector;
    a second means for detecting X-rays transmitted through the object; and
    a third means for generating a three dimensional image of the object based on X-rays detected by the second means;
    wherein:
    the first means is a means for irradiating the object with the beam of X-rays such that a focal spot of the beam of X-rays follows a non arc shaped path relative to the object; and
    the first means is a means for irradiating the object with the beam of X-rays such that a center of the beam of X-rays impinges substantially on the same location on the second means from different first means positions in the sector.

18. The system of claim 17, wherein the system comprises a mammography tomosynthesis system and the object comprises a human breast.

19. The system of claim 18, wherein the second means is a means for detecting X-rays transmitted through the object and also for moving relative to the object.

20. The system of 19, further comprising:
    an actuator configured to move the second means, wherein the second means comprises a detector; and at least one of a movable arm and combination of a rail and a motor which is configured to move the first means, wherein the first means comprises an X-ray source.

21. The system of claim 19, wherein:
the first means is a means for irradiating the object with the beam of X-rays and also for rotating in an arc shaped path in a first direction relative to the object; and
the second means is a means for detecting X-rays transmitted through the object and also for moving in a path in a second direction opposite to the first direction during rotation of the first means.

22. The system of claim 19, wherein:
the first means is a means for irradiating the object with the beam of X-rays and also for rotating in an arc shaped path in a first direction relative to the object; and
the second means is a means for detecting X-rays transmitted through the object and also for moving in an arc shaped path in a second direction opposite to the first direction.

23. The system of claim 19, wherein:
the first means is a means for irradiating the object with the beam of X-rays and also for rotating in the sector in a first direction relative to the object and for moving the X-ray beam focal spot in a y-direction; and
the second means is a means for detecting X-rays transmitted through the object and also for rotating in a direction different from the first direction.

24. The system of claim 18, wherein the first means is a means for irradiating the object with the beam of X-rays such that the focal spot of the beam of X-rays follows a non arc shaped path relative to the object.

25. The system of claim 24, wherein the first means is a means for irradiating the object with the beam of X-rays and also for rotating in a first angular direction and for moving the focal spot of the X-ray beam in a second direction substantially along a second radial direction.

26. The system of claim 24, wherein the first means is a means for irradiating the object with the beam of X-rays and also for rotating in a first angular direction for moving the focal spot of the X-ray beam in at least one of a third and fourth directions outside a plane of rotation of the first means.

27. The system of claim 18, wherein the first means is a means for irradiating the object with the beam of X-rays and also for rotating in the first angular direction and for directing a center of the X-ray beam to impinge substantially on the same location on the second means from different first means positions in the sector.

28. The system of claim 18, wherein:
the second means is a means for detecting X-rays transmitted through the object and also for moving relative to the object; and
the first means is a means for irradiating the object with the beam of X-rays such that the focal spot of the beam of X-rays follows a non arc shaped path relative to the object.

29. A tomosynthesis method of forming a three dimensional image of an object, comprising:
(a) acquiring a set of tomosynthesis projections, comprising:
moving an X-ray source along a path through a sector;
irradiating the object with a beam of X-rays from the X-ray source at a plurality of positions in the sector; and
detecting X-rays transmitted through the object with a detector; and (b) generating a three dimensional image of the object based on the detected X-rays;
wherein:
the X-ray source irradiates the object with the beam of X-rays such that the focal spot of the beam of X-rays follows a non arc shaped and non linear path; or
a center of the beam of X-rays impinges substantially on the same location on the detector from different X-ray source positions in the sector.

30. The method of claim 29, wherein the method comprises a mammography tomosynthesis method and the object comprises a human breast.

31. The method of claim 30, wherein the detector moves relative to the object during the acquisition of a set of tomosynthesis projections.

32. The method of claim 31, wherein:
the X-ray source rotates in an arc shaped path in a first direction relative to the object and periodically emits a beam of X-rays at given positions on the arc shaped path; and
the detector moves in a path in a plane in a second direction opposite to the first direction while the X-ray source rotates in the first direction.

33. The method of claim 32, wherein the detector moves in the second direction while the X-ray source emits the beam of X-rays and the X-ray source moves in the first direction.

34. The method of claim 33, wherein the detector moves in the second direction while the X-ray source does not emit the beam of X-rays and the X-ray source moves in the first direction.

35. The method of claim 32, wherein the detector moves along the path in the second direction while the X-ray source does not emit the beam of X-rays and the X-ray source moves in the first direction.

36. The method of claim 31, wherein:
the X-ray source rotates in an arc shaped path in a first direction relative to the object and periodically emits a beam of X-rays at positions on the arc shaped path; and
the detector moves in an arc shaped path in a second direction opposite to the first direction while the X-ray source rotates in the first direction.

37. The method of claim 31, wherein:
the X-ray source rotates along the path in the sector in a first angular direction relative to the object and periodically emits a beam of X-rays;
the X-ray source moves the X-ray beam focal spot in a y-direction; and
the detector rotates in a direction different from the first direction.

38. The method of claim 30, wherein the X-ray source irradiates the object with the beam of X-rays such that the focal spot of the beam of X-rays follows a non arc shaped path relative to the object.

39. The method of claim 38, wherein the X-ray source rotates along the path in a first angular direction and the focal spot of the X-ray beam moves in a second direction substantially along a second radial direction.

40. The method of claim 38, wherein the X-ray source rotates along the path in a first angular direction and the focal spot of the X-ray beam moves in at least one of third and fourth directions outside a plane of rotation of the X-ray source.

41. The method of claim 30, wherein the X-ray source rotates along the path in a first angular direction and a center of the X-ray beam impinges substantially on the same location on the detector from different X-ray source positions along a rotational path of the X-ray source.

42. The method of claim 30, wherein:
the detector moves relative to the object during the acquisition of a set of tomosynthesis projections; and
the X-ray source irradiates the object with the beam of X-rays such that the focal spot of the beam of X-rays follows a non arc shaped path relative to the object.

43. A tomosynthesis system for forming a three dimensional image of an object, comprising:
an X-ray source configured to periodically irradiate the object with a beam of X-rays, wherein the X-ray source is configured to emit the beam of X-rays while rotating and moving in a first direction along a path in a sector;
an X-ray detector positioned relative to the X-ray source to detect X-rays transmitted through the object, wherein the detector is configured to move in a second direction opposite to the first direction while the X-ray source moves in the first direction and the X-ray source emits the beam of X-rays; and
a processor which is configured to generate a three dimensional image of the object based on X-rays detected by the detector;
wherein:
the X-ray source is configured to rotate in an arc shaped path and to periodically emit the beam of X-rays from a plurality of positions along the arc shaped path; and
the X-ray source is configured to rotate at a first speed while the X-ray source emits the beam of X-rays and to rotate at a second speed higher than the first speed while the X-ray source does not emit the beam of X-rays.

44. The system of claim 43, wherein:
the detector is configured to move in the second direction to minimize maximum image blurring by at least 50% compared to image blurring if the detector does not move; and
the detector is configured to move in the first direction while the X-ray source does not emit the beam of X-rays.

45. A tomosynthesis method of forming a three dimensional image of an object, comprising:
rotating an X-ray source in a first direction in a path through a sector;
emitting a beam of X-rays from the X-ray source while the X-ray source is rotating and moving along the path in the first direction;
periodically irradiating the object with the X-ray beam;
moving a detector in a second direction opposite to the first direction while the X-ray source emits the X-ray beam and the X-ray source moves in the first direction;
detecting X-rays transmitted through the object with the detector; and
generating a three dimensional image of the object based on the detected X-rays.

46. The method of claim 45, wherein:
rotating an X-ray source in a first direction along the path through a sector comprises rotating the X-ray source in an arc shaped path at a first speed while the X-ray source emits the beam of X-rays and at a second speed higher than the first speed while the X-ray source does not emit the beam of X-rays.

47. The system of claim 46, wherein:
the detector moves in the second direction to minimize maximum image blurring by at least 50% compared to image blurring if the detector does not move; and the detector moves in the first direction while the X-ray source does not emit the beam of X-rays.

48. The method of claim 47, wherein:
the X-ray source rotates through a length of about 10 to 750 microns in the first direction along the path while the X-ray source emits one X-ray beam;
the detector moves about 5 to 60 micros in the second direction while the X-ray source emits one X-ray beam; and
beam magnification is about 1.05 to 8.

49. A tomosynthesis system for forming a three dimensional image of an object, comprising:
at least two X-ray sources configured to irradiate the object with beams of X-rays from a plurality of rotationally displaced positions along a path in a sector;
an X-ray detector positioned relative to the at least two X-ray sources and movable linearly to detect X-rays transmitted through the object; and
a processor which is configured to generate a three dimensional image of the object based on X-rays detected by the detector;
wherein the at least two X-ray sources are configured to rotate in an arc shaped path in respective at least two parallel planes and a first X-ray source is offset from a second X-ray source in a direction perpendicular to the parallel planes.

50. The system of claim 49, wherein the first X-ray source is further offset from the second X-ray source in the first direction during rotation of the first and second X-ray sources in the arc shaped path.

51. The system of claim 49, wherein the at least two X-ray sources comprise at least four stationary X-ray sources which are configured to sequentially irradiate the object with the X-ray beams.

52. A tomosynthesis system for forming a three dimensional image of an object, comprising:
an X-ray source configured to irradiate the object with a beam of X-rays from a plurality of positions along a path in a sector;
an X-ray detector positioned relative to the X-ray source to detect X-rays transmitted through the object; and
a processor which is configured to generate a three dimensional image of the object based on X-rays detected by the detector;
wherein the X-ray source is configured to rotate along the path in the sector in a first angular direction relative to the object, such that the focal spot of the X-ray beam moves in the first angular direction; and
the detector is configured to rotate in the direction different from the first angular direction.

53. A tomosynthesis system for forming a three dimensional image of an object, comprising:
an X-ray source configured to irradiate the object with a beam of X-rays from a plurality of positions along a path in a sector;
an X-ray detector positioned relative to the X-ray source to detect X-rays transmitted through the object; and
a processor which is configured to generate a three dimensional image of the object based on X-rays detected by the detector;
wherein the X-ray source is configured to rotate in an arc shaped path in a first angular direction relative to the object; and
the detector is configured to move in an arc shaped path in a second angular direction opposite to the first direction.

54. A tomosynthesis system for forming a three dimensional image of an object, comprising:
- an X-ray source configured to periodically irradiate the object with a beam of X-rays, wherein the X-ray source is configured to emit the beam of X-rays while moving in a first direction along a path in a sector;
- an X-ray detector positioned relative to the X-ray source to detect X-rays transmitted through the object, wherein the detector is configured to move in a second direction opposite to the first direction while the X-ray source moves in the first direction and the X-ray source emits the beam of X-rays; and
- a processor which is configured to generate a three dimensional image of the object based on X-rays detected by the detector, wherein:
- the X-ray source is configured to rotate in an arc shaped path and to periodically emit the beam of X-rays from a plurality of positions along the arc shaped path; and
- the X-ray source is configured to rotate at a first speed while the X-ray source emits the beam of X-rays and to rotate at a second speed higher than the first speed while the X-ray source does not emit the beam of X-rays.

55. A tomosynthesis system for forming a three dimensional image of an object, comprising:
- rotating an X-ray source in a first direction in a path through a sector;
- emitting a beam of X-rays from the X-ray source while the X-ray source is moving along the path in the first direction;
- periodically irradiating the object with the X-ray beam;
- moving a detector in a second direction opposite to the first direction while the X-ray source emits the X-ray beam and the X-ray source moves in the first direction;
- detecting X-rays transmitted through the object with the detector; and
- generating a three dimensional image of the object based on the detected X-rays, while rotating an X-ray source in a first direction along the path through a sector comprises rotating the X-ray source in an arc shaped path at a first speed while the X-ray source emits the beam of X-rays and at a second speed higher than the first speed while the X-ray source does not emit the beam of X-rays.

* * * * *